US012766131B2

(12) United States Patent
Alumkal et al.

(10) Patent No.: US 12,766,131 B2
(45) Date of Patent: Oct. 20, 2026

(54) COMPOSTIONS AND METHODS FOR TREATING PROSTATE CANCER

(71) Applicants: The Regents of the University of Michigan, Ann Arbor, MI (US); Oregon Health & Science University, Portland, OR (US)

(72) Inventors: Joshi Alumkal, Ann Arbor, MI (US); Zheng Xia, Portland, OR (US)

(73) Assignees: The Regents of the University of Michigan, Ann Arbor, MI (US); Oregon Health & Science University, Portland, OR (US)

( * ) Notice: Subject to any disclaimer, the term of this patent is extended or adjusted under 35 U.S.C. 154(b) by 623 days.

(21) Appl. No.: 18/218,930

(22) Filed: Jul. 6, 2023

(65) Prior Publication Data

US 2024/0009172 A1 Jan. 11, 2024

Related U.S. Application Data

(60) Provisional application No. 63/359,418, filed on Jul. 8, 2022.

(51) Int. Cl.

| | |
|---|---|
| ***C12Q 1/68*** | (2018.01) |
| ***A61K 31/4166*** | (2006.01) |
| ***A61P 35/00*** | (2006.01) |
| ***C12Q 1/6869*** | (2018.01) |
| ***C12Q 1/6886*** | (2018.01) |

(52) U.S. Cl.
CPC .......... *A61K 31/4166* (2013.01); *A61P 35/00* (2018.01); *C12Q 1/6869* (2013.01); *C12Q 1/6886* (2013.01); *C12Q 2600/106* (2013.01); *C12Q 2600/158* (2013.01)

(58) Field of Classification Search
None
See application file for complete search history.

(56) References Cited

PUBLICATIONS

Aggarwal et al. 2018. J Clin Oncol 36:2492-2503. (Year: 2018).*
Abate-Shen et al. Molecular genetics of prostate cancer. Genes Dev. Oct. 1, 2000;14(19):2410-34.
Abdulfatah, E., et al. De novo neuroendocrine transdifferentiation in primary prostate cancer-a phenotype associated with advanced clinico-pathologic features and aggressive outcome. Med Oncol. Feb. 14, 2021;38(3):26.
Abida, W., et al. Genomic correlates of clinical outcome in advanced prostate cancer. Proc Natl Acad Sci U S A. Jun. 4, 2019;116(23):11428-11436.
Adalsteinsson, V.A., et al. Scalable whole-exome sequencing of cell-free DNA reveals high concordance with metastatic tumors. Nat Commun. Nov. 6, 2017;8(1):1324.
Aggarwal, R., et al. Clinical and Genomic Characterization of Treatment-Emergent Small-Cell Neuroendocrine Prostate Cancer: A Multi-institutional Prospective Study. J Clin Oncol. Aug. 20, 2018;36(24):2492-2503.
Aggarwal, R.R., et al. A Phase Ib/IIa Study of the Pan-BET Inhibitor ZEN-3694 in Combination with Enzalutamide in Patients with Metastatic Castration-resistant Prostate Cancer. Clin Cancer Res. Oct. 15, 2020;26(20):5338-5347.
Alumkal, J.J., et al. Transcriptional profiling identifies an androgen receptor activity-low, stemness program associated with enzalutamide resistance. Proc Natl Acad Sci U S A. Jun. 2, 2020;117(22):12315-12323.
Alvarez, M.J., et al. Functional characterization of somatic mutations in cancer using network-based inference of protein activity. Nat Genet. Aug. 2016;48(8):838-47.
Annala, M., et al. Circulating Tumor DNA Genomics Correlate with Resistance to Abiraterone and Enzalutamide in Prostate Cancer. Cancer Discov. Apr. 2018;8(4):444-457.
Armstrong, A.J., et al. Arches: A Randomized, Phase III Study of Androgen Deprivation Therapy With Enzalutamide or Placebo in Men With Metastatic Hormone-Sensitive Prostate Cancer. J Clin Oncol. Nov. 10, 2019;37(32):2974-2986.
Armstrong, A.J., et al. Prospective Multicenter Study of Circulating Tumor Cell AR-V7 and Taxane Versus Hormonal Treatment Outcomes in Metastatic Castration-Resistant Prostate Cancer. JCO Precis Oncol. Oct. 28, 2020:4:PO.20.00200.
Attard, G., et al. Phase I clinical trial of a selective inhibitor of CYP17, abiraterone acetate, confirms that castration-resistant prostate cancer commonly remains hormone driven. Eur Urol. Jul. 2009;56(1):220.
Bankhead, P., et al. QuPath: Open source software for digital pathology image analysis. Sci Rep. Dec. 4, 2017;7(1):16878.
Beer, T.M., et al. Enzalutamide in metastatic prostate cancer before chemotherapy. N Engl J Med. Jul. 31, 2014;371(5):424-33.
Beltran, H., et al. Divergent clonal evolution of castration-resistant neuroendocrine prostate cancer. Nat Med. Mar. 2016;22(3):298-305.
Beltran, H., et al. The role of lineage plasticity in prostate cancer therapy resistance. Clin Cancer Res. Dec. 1, 2019;25(23):6916-6924.
Bluemn, E.G., et al. Androgen Receptor Pathway-Independent Prostate Cancer Is Sustained through FGF Signaling. Cancer Cell. Oct. 9, 2017;32(4):474-489.e6.
Cejas, P., et al. Subtype heterogeneity and epigenetic convergence in neuroendocrine prostate cancer. Nat Commun. Oct. 1, 2021;12(1):5775.
Chen, W.S., et al. Genomic Drivers of Poor Prognosis and Enzalutamide Resistance in Metastatic Castration-resistant Prostate Cancer. Eur Urol. Nov. 2019;76(5):562-571.
Chen, W.S., et al. Novel RB1-Loss Transcriptomic Signature Is Associated with Poor Clinical Outcomes across Cancer Types. Clin Cancer Res. Jul. 15, 2019;25(14):4290-4299.
Clegg, N.J., et al. ARN-509: a novel antiandrogen for prostate cancer treatment. Cancer Res. Mar. 15, 2012;72(6):1494-503.
Davis, I.D., et al. Enzalutamide with Standard First-Line Therapy in Metastatic Prostate Cancer. N Engl J Med. Jul. 11, 2019;381(2):121-131.

(Continued)

*Primary Examiner* — Juliet C Switzer
(74) *Attorney, Agent, or Firm* — Casimir Jones, S.C.; Tanya A. Arenson

(57) ABSTRACT

The present disclosure relates to compositions, systems, and methods for treating cancer. In particular, the present disclosure relates to compositions, systems, and methods for characterizing and treating prostate cancer (e.g., castration-resistant prostate cancer).

5 Claims, 7 Drawing Sheets

(56) References Cited

PUBLICATIONS

Donehower, L.A., et al. Integrated Analysis of TP53 Gene and Pathway Alterations in The Cancer Genome Atlas. Cell Rep. Jul. 30, 2019;28(5):1370-1384.e5.
Foye, A. et al. Cancer gene profiling in prostate cancer. Methods Mol Biol. 2010:576:293-326.
Ge, J., et al. Ubiquitin carboxyl-terminal hydrolase isozyme L5 inhibits human glioma cell migration and invasion via downregulating SNRPF. Oncotarget. Dec. 7, 2017;8(69):113635-113649.
Grasso, C., et al. Assessing copy number alterations in targeted, amplicon-based next-generation sequencing data. J Mol Diagn. Jan. 2015;17(1):53-63.
Guan, S.S., et al. ATP synthase subunit-beta down-regulation aggravates diabetic nephropathy. Sci Rep. Oct. 9, 2015:5:14561.
He, M.X., et al. Transcriptional mediators of treatment resistance in lethal prostate cancer. Nat Med. Mar. 2021;27(3):426-433.
Hovelson, D.H., et al. Development and validation of a scalable next-generation sequencing system for assessing relevant somatic variants in solid tumors. Neoplasia. Apr. 2015;17(4):385-99.
Hovelson, D.H., et al. Rapid, ultra low coverage copy number profiling of cell-free DNA as a precision oncology screening strategy. Oncotarget. Sep. 22, 2017;8(52):89848-89866.
Kim, D.H., et al. BET Bromodomain Inhibition Blocks an AR-Repressed, E2F1-Activated Treatment-Emergent Neuroendocrine Prostate Cancer Lineage Plasticity Program. Clin Cancer Res. Sep. 1, 2021;27(17):4923-4936.
Ku, S.Y., et al. Rb1 and Trp53 cooperate to suppress prostate cancer lineage plasticity, metastasis, and antiandrogen resistance. Science. Jan. 6, 2017;355(6320):78-83.
Labrecque, M.P., et al. Molecular profiling stratifies diverse phenotypes of treatment-refractory metastatic castration-resistant prostate cancer. J Clin Invest. Jul. 30, 2019;129(10):4492-4505.
Lee, J.K., et al. N-Myc Drives Neuroendocrine Prostate Cancer Initiated from Human Prostate Epithelial Cells. Cancer Cell. Apr. 11, 2016;29(4):536-547.
Lefebvre, C., et al. A human B-cell interactome identifies MYB and FOXM1 as master regulators of proliferation in germinal centers. Mol Syst Biol. Jun. 8, 2010:6:377.
Li, B. et al. RSEM: accurate transcript quantification from RNA-Seq data with or without a reference genome. BMC Bioinformatics. Aug. 4, 2011:12:323.
Lin, D., et al. High fidelity patient-derived xenografts for accelerating prostate cancer discovery and drug development. Cancer Res. Feb. 15, 2014;74(4):1272-83.
Lo, U.G., et al. IFNgamma-Induced IFIT5 Promotes Epithelial-to-Mesenchymal Transition in Prostate Cancer via miRNA Processing. Cancer Res. Mar. 15, 2019;79(6):1098-1112.
Love, M.I., Huber, W. & Anders, S. Moderated estimation of fold change and dispersion for RNA-seq data with DESeq2. Genome Biol. 2014;15(12):550.
Mckay, R.R., et al. Phase II Multicenter Study of Enzalutamide in Metastatic Castration-Resistant Prostate Cancer to Identify Mechanisms Driving Resistance. Clin Cancer Res. Jul. 1, 2021;27(13):3610-3619.
Miyamoto, D.T., et al. RNA-Seq of single prostate CTCs implicates noncanonical Wnt signaling in antiandrogen resistance. Science. Sep. 18, 2015;349(6254):1351-6.
Mu, P., et al. SOX2 promotes lineage plasticity and antiandrogen resistance in TP53- and RB1-deficient prostate cancer. Science. Jan. 6, 2017;355(6320):84-88.
Nyquist, M.D., et al. Combined TP53 and RB1 Loss Promotes Prostate Cancer Resistance to a Spectrum of Therapeutics and Confers Vulnerability to Replication Stress. Cell Rep. May 26, 2020;31(8):107669.
Pal, S.K., et al. Identification of mechanisms of resistance to treatment with abiraterone acetate or enzalutamide in patients with castration-resistant prostate cancer (CRPC). Cancer. Mar. 15, 2018;124(6):1216-1224.
Penson, D.F., et al. Enzalutamide Versus Bicalutamide in Castration-Resistant Prostate Cancer: The STRIVE Trial. J Clin Oncol. Jun. 20, 2016;34(18):2098-106.
Rak, M. et al. Supernumerary subunits NDUFA3, NDUFA5 and NDUFA12 are required for the formation of the extramembrane arm of human mitochondrial complex I. FEBS Lett. May 2, 2014;588(9):1832-8.
Robertson, A.G., et al. Integrative Analysis Identifies Four Molecular and Clinical Subsets in Uveal Melanoma. Cancer Cell. Aug. 14, 2017;32(2):204-220.e15.
Ruijter et al., Molecular Genetics and Epidemiology of Prostate Carcinoma. Endocrine Reviews, vol. 20, Issue 1, Feb. 1, 1999, pp. 22-45.
Scher, H.I., et al. Antitumour activity of MDV3100 in castration-resistant prostate cancer: a phase 1-2 study. Lancet. Apr. 24, 2010;375(9724):1437-46.
Scher, H.I., et al. Increased survival with enzalutamide in prostate cancer after chemotherapy. N Engl J Med. Sep. 27, 2012;367(13):1187-97.
Shore, N.D., et al. Efficacy and safety of enzalutamide versus bicalutamide for patients with metastatic prostate cancer (TERRAIN): a randomised, double-blind, phase 2 study. Lancet Oncol. Feb. 2016;17(2):153-163.
Swami, U., et al. Advanced Prostate Cancer: Treatment Advances and Future Directions. Trends Cancer. Aug. 2020;6(8):702-715.
Tao, D.L., et al. Molecular Testing in Patients With Castration-Resistant Prostate Cancer and Its Impact on Clinical Decision Making. JCO Precis Oncol. 2017:1:PO.16.00067.
Tran, C., et al. Development of a second-generation antiandrogen for treatment of advanced prostate cancer. Science. May 8, 2009;324(5928):787-90.
Wang, Y., et al. Molecular events in neuroendocrine prostate cancer development. Nat Rev Urol. Oct. 2021;18(10):581-596.
Wu, D. et al. Camera: a competitive gene set test accounting for inter-gene correlation. Nucleic Acids Res. Sep. 1, 2012;40(17):e133.
Xin, Z., et al. Insulinoma-associated protein 1 is a novel sensitive and specific marker for small cell carcinoma of the prostate. Hum Pathol. Sep. 2018:79:151-159.
Yamashina, T., et al. Cancer stem-like cells derived from chemoresistant tumors have a unique capacity to prime tumorigenic myeloid cells. Cancer Res. May 15, 2014;74(10):2698-709.
Yu, J., et al. The Functional Landscape of Patient-Derived RNF43 Mutations Predicts Sensitivity to Wnt Inhibition. Cancer Res. Dec. 15, 2020;80(24):5619-5632.
Zhang, D., et al. Stem cell and neurogenic gene-expression profiles link prostate basal cells to aggressive prostate cancer. Nat Commun. Feb. 29, 2016:7:10798.
Zhang, X., et al. Tiki1 is required for head formation via Wnt cleavage-oxidation and inactivation. Cell. Jun. 22, 2012;149(7):1565-77.

* cited by examiner

COMPOSTIONS AND METHODS FOR TREATING PROSTATE CANCER

STATEMENT OF RELATED APPLICATIONS

This application claims the benefit of U.S. Provisional Patent Application No. 63/359,418, filed Jul. 8, 2022, the contents of each of which are incorporated by reference herein.

FIELD OF THE DISCLOSURE

The present disclosure relates to compositions, systems, and methods for treating cancer. In particular, the present disclosure relates to compositions, systems, and methods for characterizing and treating prostate cancer (e.g., castration-resistant prostate cancer).

BACKGROUND OF THE DISCLOSURE

Afflicting one out of nine men over age 65, prostate cancer (PCA) is a leading cause of male cancer-related death, second only to lung cancer (Abate-Shen and Shen, Genes Dev 14:2410 [2000]; Ruijter et al., Endocr Rev, 20:22 [1999]). The American Cancer Society estimates that about 184,500 American men will be diagnosed with prostate cancer and 39,200 will die in 2001.

Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, while amounts above 50 may show that the tumor has spread elsewhere in the body.

When PSA or digital tests indicate a strong likelihood that cancer is present, a transrectal ultrasound (TRUS) is used to map the prostate and show any suspicious areas. Biopsies of various sectors of the prostate are used to determine if prostate cancer is present. Treatment options depend on the stage of the cancer. Men with a 10-year life expectancy or less who have a low Gleason number and whose tumor has not spread beyond the prostate are often treated with watchful waiting (no treatment). Treatment options for more aggressive cancers include surgical treatments such as radical prostatectomy (RP), in which the prostate is completely removed (with or without nerve sparing techniques) and radiation, applied through an external beam that directs the dose to the prostate from outside the body or via low-dose radioactive seeds that are implanted within the prostate to kill cancer cells locally. Anti-androgen hormone therapy is also used, alone or in conjunction with surgery or radiation. Hormone therapy uses luteinizing hormone-releasing hormones (LH-RH) analogs, which block the pituitary from producing hormones that stimulate testosterone production. Patients must have injections of LH-RH analogs for the rest of their lives.

While surgical and hormonal treatments are often effective for localized PCA, advanced disease remains essentially incurable. Androgen ablation is the most common therapy for advanced PCA, leading to massive apoptosis of androgen-dependent malignant cells and temporary tumor regression. In most cases, however, the tumor reemerges with a vengeance and can proliferate independent of androgen signals.

What is needed are improved methods for identifying and treating cancer unlikely to respond to androgen ablation.

SUMMARY OF THE DISCLOSURE

The present disclosure relates to compositions, systems, and methods for treating cancer. In particular, the present disclosure relates to compositions, systems, and methods for characterizing and treating prostate cancer (e.g., castration-resistant prostate cancer).

Experiments described herein identified a gene expression signature that identifies individuals unlikely to respond to androgen deprivation therapy. Such individuals can be offered alternative treatments, thus improving outcomes.

Accordingly, in some embodiments, provided herein is a method for treating prostate cancer, comprising: a) assaying a sample from a subject diagnosed with prostate cancer for the level of expression of one or more (e.g., 1, 2, 3, 4, 5, 6, 7, 8, 9, 10, 11, 12, 13, or all) genes selected from RNF43, SNRPF, TRABD2A, NDUFA12, GAS2L3, RPS24, DNA2, RP5-857K21.10, POC1B, ADK, ATPSB, XPOT, SLCO1B3, or RHOBTB1; b) calculating a lineage plasticity score based on the level of gene expression; c) identifying subjects with a high lineage plasticity score; and d) administering a non-androgen receptor signaling inhibitor treatment to the subjects. In some embodiments, a score above 0.577 (e.g., above 0.45, 0.50, 0.55, 0.60, or 0.65) (e.g., as calculated using GSVA), is considered high.

The present disclosure is not limited to particular non-androgen receptor signaling inhibitor treatment. Examples include but are not limited to, chemotherapy, radiation, surgery, or a pharmaceutical agent. In some exemplary embodiments, the treatment is an agent that blocks expression or activity of one or more of the genes. Examples include but are not limited to, an antibody, a nucleic acid, or a small molecule.

Further embodiments provide a method for treating prostate cancer, comprising: a) assaying a sample from a subject diagnosed with prostate cancer for the level of expression of one or more (e.g., 1, 2, 3, 4, 5, 6, 7, 8, 9, 10, 11, 12, 13, or all) genes selected from RNF43, SNRPF, TRABD2A, NDUFA12, GAS2L3, RPS24, DNA2, RP5-857K21.10, POC1B, ADK, ATPSB, XPOT, SLCO1B3, or RHOBTB1; b) calculating a lineage plasticity score based on the level of gene expression; c) identifying subjects with a low lineage plasticity score; and d) administering an androgen receptor signaling inhibitor treatment (e.g., enzalutamide) to the subjects.

Additional embodiments provide a method for measuring gene expression, comprising: a) assaying a sample from a subject diagnosed with prostate cancer for the level of expression of two or more genes (e.g., 2, 3, 4, 5, 6, 7, 8, 9, 10, 11, 12, 13, or all) selected from RNF43, SNRPF, TRABD2A, NDUFA12, GAS2L3, RPS24, DNA2, RP5-857K21.10, POC1B, ADK, ATPSB, XPOT, SLCO1B3, or RHOBTB1; b) calculating a lineage plasticity score based on the level of gene expression.

Some embodiments provide a method for measuring gene expression, comprising: assaying a sample from a subject diagnosed with prostate cancer for the level of expression of two or more genes (e.g., 2, 3, 4, 5, 6, 7, 8, 9, 10, 11, 12, 13, or all) selected from RNF43, SNRPF, TRABD2A, NDUFA12, GAS2L3, RPS24, DNA2, RP5-857K21.10, POC1B, ADK, ATPSB, XPOT, SLCO1B3, or RHOBTB1.

In some embodiments, the level of expression of no more than 14, 20, 25, 30, 500, or 100 genes are detected. In some embodiments, the level of expression of only RNF43, SNRPF, TRABD2A, NDUFA12, GAS2L3, RPS24, DNA2, RP5-857K21.10, POC1B, ADK, ATPSB, XPOT, SLCO1B3, and RHOBTB1 is detected.

Yet other embodiments provide a method for providing a prognosis to a subject with prostate cancer, comprising: a) assaying a sample from a subject diagnosed with prostate cancer for the level of expression of one or more (e.g., 1, 2, 3, 4, 5, 6, 7, 8, 9, 10, 11, 12, 13, or all) genes selected from RNF43, SNRPF, TRABD2A, NDUFA12, GAS2L3, RPS24, DNA2, RP5-857K21.10, POC1B, ADK, ATPSB, XPOT, SLCO1B3, or RHOBTB1; b) calculating a lineage plasticity score based on the level of gene expression; and c) providing a prognosis of increased likelihood of death when the lineage plasticity score is high.

Still other embodiments provide a method for characterizing prostate cancer a subject with prostate cancer, comprising: a) assaying a sample from a subject diagnosed with prostate cancer for the level of expression of one or more (e.g., 1, 2, 3, 4, 5, 6, 7, 8, 9, 10, 11, 12, 13, or all) genes selected from RNF43, SNRPF, TRABD2A, NDUFA12, GAS2L3, RPS24, DNA2, RP5-857K21.10, POC1B, ADK, ATPSB, XPOT, SLCO1B3, or RHOBTB1; b) calculating a lineage plasticity score based on the level of gene expression; and c) providing a prognosis of increased likelihood of said cancer undergoing lineage plasticity when the lineage plasticity score is high.

In some embodiments, the prostate cancer is castration-resistant prostate cancer (CRPC). In some embodiments, the sample is blood, urine or prostate cells.

Also provided is a kit, comprising reagents for detecting the level of expression of one or more (e.g., 1, 2, 3, 4, 5, 6, 7, 8, 9, 10, 11, 12, 13, or all) genes selected from RNF43, SNRPF, TRABD2A, NDUFA12, GAS2L3, RPS24, DNA2, RP5-857K21.10, POC1B, ADK, ATPSB, XPOT, SLCO1B3, or RHOBTB1. In some embodiments, the reagents are nucleic acid primers, nucleic acid probes, or antibodies.

Additional embodiments provide a system, comprising: a computer processor and computer software configured to calculate a lineage plasticity score based on the level of expression of one or more (e.g., 1, 2, 3, 4, 5, 6, 7, 8, 9, 10, 11, 12, 13, or all) genes selected from RNF43, SNRPF, TRABD2A, NDUFA12, GAS2L3, RPS24, DNA2, RP5-857K21.10, POC1B, ADK, ATPSB, XPOT, SLCO1B3, or RHOBTB1.

Also provided is the use of an androgen receptor signaling inhibitor to treat prostate cancer in a subject with a low lineage plasticity score.

Additional embodiments will be apparent to persons skilled in the relevant art based on the teachings contained herein.

DEFINITIONS

Figure 1:
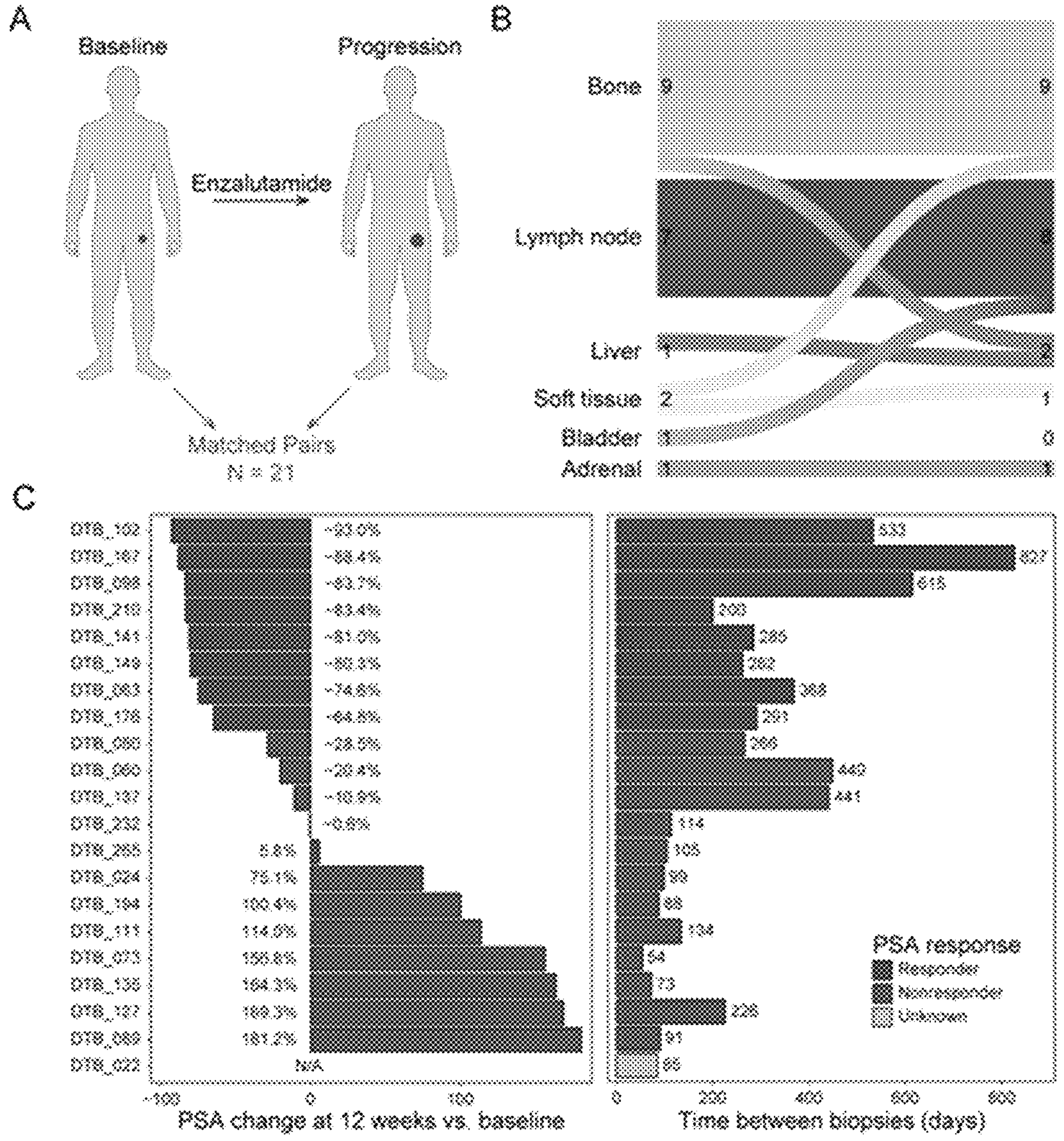
FIG. 1 shows study biopsy and clinical information. a. Study schematic. b. Sankey diagram showing site of biopsy at baseline (left) and at progression (right). c. Left panel shows PSA change at 12 weeks for each patient.

To facilitate an understanding of the present disclosure, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. As used herein, the term "metastasized prostate cancer cells" is meant to refer to prostate cancer cells which have metastasized.

The term "neoplasm" as used herein refers to any new and abnormal growth of tissue. Thus, a neoplasm can be a non-malignant neoplasm, a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, 0-D-mannosylqueosine, 5'-methoxycarbonylmethyluracil, 5-methoxyuracil, 2-methylthio-N-isopentenyladenine, uracil-acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example, a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., 1-1±, NH 4+, Nat, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF THE DISCLOSURE

The present disclosure relates to compositions, systems, and methods for treating cancer. In particular, the present disclosure relates to compositions, systems, and methods for characterizing and treating prostate cancer (e.g., castration-resistant prostate cancer).

Androgen deprivation therapy (ADT) is the principal treatment for metastatic prostate cancer, but progression to castration-resistant prostate cancer (CRPC) is nearly universal. In recent years, potent inhibitors of the androgen receptor (AR)—a luminal lineage transcription factor—have been developed, including the AR antagonist enzalutamide (enza) 1-5. Enza improves progression-free survival and overall survival in patients with CRPC; further, enza also increases overall survival in patients with hormone-naïve prostate cancer who are beginning ADT for the first time 6-9. However, one-third of patients do not respond, and those with de novo resistance have a significantly increased risk of death compared to responders 6-9.

Despite intense study, clinical enza resistance remains poorly understood. Several studies examined mechanisms of de novo or acquired enza resistance in clinical samples and implicated: AR amplification,10,11 AR splice variants,12,13 increased Wnt/r3-catenin signaling,14-16 increased TGF-β signaling,15,17 epithelial to mesenchymal transition or increased stemness,15,18 and lineage plasticity 15. However, these prior studies were largely restricted to DNA mutational profiling, compared baseline and progression samples from different patients, used limited numbers of matched samples, or did not focus on transcriptional changes.

Reports have indicated that most CRPC tumors resistant to AR signaling inhibitors (ARSIs) continue to depend on the AR 18,19. However, lineage plasticity 20—most commonly exemplified by loss of AR signaling and a switch from a luminal to an alternate differentiation program—is a resistance mechanism that appears to be increasing in the era of more widespread use of ARSIs. The emergence of tumors with features of lineage plasticity may occur through diverse mechanisms: selection of a pre-existing clone that has already undergone differentiation change, acquisition of new genetic alterations that promote differentiation change, or transdifferentiation of tumor cells through epigenetic mechanisms 18, 21-23.

Lineage plasticity is a continuum, ranging from tumors with persistent AR expression but low AR activity, those that lose AR expression but do not undergone neuroendocrine differentiation (double negative prostate cancer (DNPC)), and those that lose AR expression and do undergo neuroendocrine differentiation (neuroendocrine prostate cancer (NEPC) 24. Importantly, CRPC tumors that have undergone lineage plasticity are associated with a much shorter survival than CRPC tumors that have persistent AR activity and a luminal lineage program, demonstrating an urgent need to understand treatment-induced lineage plasticity in prostate cancer 25.

Experiments described herein compared gene expression profiles between matched CRPC tumor biopsy samples prior to enza and at the time of progression to identify pre-treatment and treatment-induced resistance mechanisms in individual patients. Results from 21 matched samples demonstrated key transcriptional differences, including lineage plasticity changes induced by enza, that contribute to resistance.

Accordingly, provided herein are compositions and methods for characterizing and treating prostate cancer. In some embodiments, the compositions and methods of the present disclosure utilize a 14 gene signature of lineage plasticity to identify subjects most likely to benefit from AR targeted therapy. In some embodiments, the level of expression of the lineage plasticity signature (e.g., one or more (e.g., 1, 2, 3, 4, 5, 6, 7, 8, 9, 10, 11, 12, 13, or all) of RNF43, SNRPF, TRABD2A, NDUFA12, GAS2L3, RPS24, DNA2, RP5-857K21.10, POC1B, ADK, ATPSB, XPOT, SLCO1B3, or RHOBTB1 is utilized to calculate a lineage plasticity score.

In some embodiments, lineage plasticity scores are calculated using gene expression data. In some embodiments, the single-sample gene set enrichment analysis (ssGSEA) 8 implemented in the GSVA 9 R package is used to calculate the score.

In some embodiments, a numerical cut-off for a "high" lineage plasticity score is utilized. For example, in some embodiments, a score above 0.577 (e.g., above 0.45, 0.50, 0.60, or 0.65) (e.g., as calculated using GSVA or other method), is considered high.

The present invention is not limited to particular methods of detecting the level of the recited markers. Markers may be detected as DNA (e.g., cDNA), RNA (e.g., mRNA), or protein.

In some embodiments, nucleic acid sequencing methods are utilized for detection. In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.,* 55: 641-658, 2009; MacLean et al., *Nature Rev. Microbiol.,* 7: 287-296; each herein incorporated by reference in their entirety). NGS methods can be broadly divided into those that typically use template amplification and those that do not Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In some embodiments, hybridization methods are utilized. Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with radio-, fluorescent- or antigen-labeled bases is localized and quantitated in the tissue using autoradiography, fluorescence microscopy or immunohistochemistry. ISH can also use two or more probes, labeled with radioactivity or the other non-radioactive labels, to simultaneously detect two or more transcripts.

In some embodiments, markers are detected using fluorescence in situ hybridization (FISH). The preferred FISH assays for methods of embodiments of the present disclosure utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

Different kinds of biological assays are called microarrays including, but not limited to: microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limited to: printing with fine-pointed pins onto glass slides; photolithography using pre-made masks; photolithography using dynamic micromirror devices; ink-jet printing; or, electrochemistry on microelectrode arrays.

Southern and Northern blotting may be used to detect specific DNA or RNA sequences, respectively. In these techniques DNA or RNA is extracted from a sample, fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

In some embodiments, marker sequences are amplified (e.g., after conversion to DNA) prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

In some embodiments, quantitative evaluation of the amplification process in real-time is performed. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs, including fluorescence resonance energy transfer (FRET) labels, are disclosed in, for example U.S. Pat. Nos. 6,534,274 and 5,776,782, each of which is herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed, for example, in U.S. Pat. Nos. 5,925,517 and 6,150,097, herein incorporated by reference in its entirety.

The cancer marker genes described herein may be detected as proteins using a variety of protein techniques known to those of ordinary skill in the art, including but not limited to: protein sequencing; and, immunoassays.

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays. Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

Embodiments of the present invention further provide kits and systems comprising reagents for detection of the recited markers (e.g., primer, probes, etc.). In some embodiments, kits and systems comprise computer systems for analyzing marker levels and providing a lineage plasticity score, diagnoses, prognoses, or determining treatment courses of action.

In some embodiments, a computer-based analysis program is used to translate the raw data generated by the detection assay (e.g., levels of the recited markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine or blood sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication system). Once received by the profiling service, the sample is processed and a profile is produced (i.e., marker levels) specific for the diagnostic or prognostic information desired for the subject.

The profile data is then prepared in a format suitable for interpretation by a treating clinician. For example, rather than providing raw data, the prepared format may represent a diagnosis or risk assessment (e.g., level of markers) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research. For example, the data may be used to further optimize the inclusion or elimination of markers as useful indicators of a particular condition or stage of disease or as a companion diagnostic to determine a treatment course of action.

In some specific embodiments, the lineage plasticity score described herein finds use in characterizing, prognosing, and treating prostate cancer. For example, in some embodiments, the score is used to identify individuals likely to develop lineage plasticity (e.g., individuals with a high lineage plasticity score) and corresponding resistance to AR blocking therapy such as enza. Such individuals are offered alternative therapies (e.g., surgery, radiation, chemotherapy, immune therapy, or agents targeted to the genes in the lineage plasticity signature).

Conversely, individuals with a low lineage plasticity score are likely to respond to AR blocking therapy and are thus offered an AR blocking therapy such as enza or other hormone therapy.

Additional hormonal therapies include but are not limited to, leuprolide, goserelin, triptorelin, leuprolide mesylate, degarelix, relugolix, abiraterone, ketoconazole, flutamide, bicalutamide, nilutamide, apalutamide, and darolutamide.

Examples of chemotherapy used in prostate cancer include but are not limited to, docetaxel, cabazitaxel, mitoxantrone, and estramustine. Examples of immnotherapy used in prostate cancer include but are not limited to, cancer vaccines (e.g., sipuleucel-T) and immune checkpoint inhibitors (e.g., pembrolizumab). Additional prostate cancer treatments include but are not limited to, PARP inhibitors (e.g., rucaparib and olaparib).

In some embodiments, a high lineage plasticity score is indicative of an individual with an increased likelihood of death from prostate cancer. In some embodiments, such individuals are offered more aggressive treatments.

As described above, in some embodiments, the present disclosure provides agents that target (e.g., inhibit the expression or one or more activities of) a gene in a lineage plasticity signature. Examples include but are not limited to, small molecules, nucleic acids, and antibodies.

In some embodiments, the inhibitor is a nucleic acid. Exemplary nucleic acids suitable for inhibiting expression of the described markers (e.g., by preventing expression of the marker) include, but are not limited to, antisense nucleic acids and RNAi. In some embodiments, nucleic acid therapies are complementary to and hybridize to at least a portion (e.g., at least 5, 8, 10, 11, 12, 13, 14, 15, 16, 17, 18, 19, or 20 nucleotides) of a marker described herein.

In some embodiments, compositions comprising oligomeric antisense compounds, particularly oligonucleotides are used to modulate the function of nucleic acid molecules encoding a marker described herein, ultimately modulating the amount of marker gene expressed. This is accomplished by providing antisense compounds that specifically hybridize with one or more nucleic acids encoding the marker genes. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is decreasing the amount of marker expressed.

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

In some embodiments, one or more targeted therapies are administered in combination with an existing therapy for prostate cancer.

In some embodiments, agents described herein are screening for activity against prostate cancer (e.g., in vitro drug screening assays or in a clinical study).

EXPERIMENTAL

The following examples are provided in order to demonstrate and further illustrate certain preferred embodiments and aspects of the present disclosure and are not to be construed as limiting the scope thereof.

Example 1

Methods

West Coast Dream Team (WCDT) Metastatic Tissue Collection

Methods for tissue collection have been described previously 48. RNA-sequencing was performed on matched, paired biopsies from 21 men with metastatic, castration-resistant prostate cancer who had a tissue biopsy performed prior to starting treatment with enza and a second biopsy performed at time of progression.

RNA-Sequencing and Data Processing

Core biopsy samples were flash frozen in Optical Cutting Temperature (OCT) for gene expression analysis. Laser capture microdissection was performed on frozen sections to enrich for tumor content 49. Total RNA was isolated (Stratagene Absolutely RNA Nano Prep) (RIN>8) and amplified using NuGEN Ovation RNA seq System V2. Libraries were generated using NuGEN Ovation Ultralow System V2 for Illumina sequencing. RNA seq was performed on the Illumina NextSeq 500, PE75 with at least 100M read pairs. The raw fastq files were first quality checked using FastQC (version 0.11.8) software (http://www.bioinformatics.bbsrc.ac.uk/projects/fastqc/). Fastq files were aligned to hg38 human reference genome and per-gene counts and transcripts per million (TPM) quantified by RSEM 50 (version 1.3.1) based on the gene annotation gencode.v28.annotation.gtf.

Unsupervised Clustering

To understand the overall transcriptional similarities across these 21 paired samples, unsupervised clustering was performed using RNA-sequencing data. Briefly, the raw count matrix was filtered to remove low expression genes and genes with raw count >=20 in at least two samples were kept. The filtered count matrix was transformed using the vst function implemented in DESeq2 R package (version 1.22.2) 51. The transformed values were used to compute the sample-to-sample Euclidean distance metric for hierarchical clustering through the 'complete' method. To cluster samples prior to treatment (baseline), TPM gene expression data was first filtered to remove low expression genes as described above and non-protein-coding genes as annotated by HUGO Gene Nomenclature Committee (HGNC). The filtered TPM matrix was log transformed and the 500 most varying genes were selected to compute the sample-to-sample gene expression spearman correlation which was then converted to distance followed by clustering through the 'complete-linkage hierarchical clustering' method.

Differential Expression Gene, Pathway, and Master Regulator Analysis

Differential gene expression analysis was performed using DESeq2 (version 1.22.2). Gene expression differences were considered significant if passing the following criteria: adjusted P-value <0.05, absolute fold change >1.5. For the converter vs non-converter baseline sample comparison, we used the adjusted P-value <0.1. The Wald test statistics from DESeq2 output was used as pre-ranked gene list scores to perform pathway analysis using cameraPR implemented in limma R package (version 3.38.3) 52 and the hallmark collection from MSigDB database (version 7.0). Transcription factor activity was inferred using the master regulator inference algorithm 53 (MARINa) implemented in the viper R package (version 1.16.0) 26. Pre-ranked gene list scores and a regulatory network (regulome) are the two sources of data required as input for viper analysis. The pre-ranked gene list scores were the same as above and the transcription factor regulome used in this study was curated from several databases as previously described 54.

Single Sample AR Activity

To measure single-sample AR regulon activity, the viper R package (version 1.16.0) 26 with the log2 transformed TPM gene expression matrix as input was used. The regulon used in viper analysis was the same as described above. Scores were considered to have marked difference if change between baseline and progression sample was >20% of the range between all samples.

Multiplex Immunofluorescence

Multiplex immunofluorescence studies using AR—(Cell signaling Technologies, 5153T), INSM1—(Santa Cruz, sc-271408), NKX3.1—(Fisher, 5082788) and HOXB13—(Cell signaling Technologies, 90944S) specific antibodies were carried out on archival formalin fixed paraffin embedded (FFPE) tissues. In brief, 5 μM paraffin sections were de-waxed and rehydrated following standard protocols. The staining protocol consisted of four sequential staining steps, each with tyramide-based signal amplification using the Tyramide SuperBoost kits (Thermo Fisher) as described previously 55. De-waxed slides were first subjected to steaming for 40 min in Target Retrieval Solution (S1700, Agilent) and incubated with AR specific antibodies (1:00). Signal amplification was carried out by first incubating slides with PowerVision Poly-AP Anti-Rabbit (Leica) secondary antibodies followed by Tyramide568 (Tyramide SuperBoost kit, Thermo Fisher) according to manufacturer's protocols. Slides were then stripped by steaming in citrate buffer (Vector) for 20 minutes and subsequently incubated with INSM1 specific antibodies (1:50) followed by PowerVision Poly-AP Anti-mouse (Leica) secondary antibodies and Tyramide647 (Tyramide SuperBoost kit). Next, slides were stripped for 20 minutes in Target Retrieval Solution (S1700, Agilent), incubated with NKX3.1 specific antibodies (1:200) followed by PowerVision Poly-AP Anti-rabbit (Leica) secondary antibodies and Tyramide488 (Tyramide SuperBoost kit). Lastly, slides were steamed in in Citrate buffer (Vector) for 20 minutes, incubated with HOXB13 antibodies (1:50) followed by PowerVision Poly-AP Anti-rabbit (Leica) secondary antibodies and Tyramide350 (Tyramide SuperBoost kit). Slides were mounted with Prolong (Thermo Fisher), imaged on a Nikon Eclipse E800 (Nikon) microscope and image analyses were carried out using QuPath (v0.3.0) 56.

DNA-Sequencing

Next generation targeted genomic DNA-sequencing of FFPE tissue was performed using a 124 gene as previously described 57. Cell-free DNA was extracted from approximately 1 mL of previously banked plasma and subjected to low-pass whole-genome-sequencing (WGS) and targeted deep sequencing using the Ion Torrent™ Next-Generation Sequencing (NGS) system (Thermo Fisher Scientific, Waltham, MA), as described previously 58. NGS reads were processed using Ion Torrent Suite™ and analyzed with standard workflows in Ion Reporter™ (Thermo Fisher Scientific) and established in-house bioinformatics pipelines. Tumor content estimates were derived from low-pass WGS data using the ichorCNA package in R 59. Total mapped NGS reads for low-pass WGS ranged from 4,235,342-6,185,948 (corresponding to 0.202-0.292× coverage). Targeted deep sequencing was performed using the Oncomine™ Comprehensive Assay Plus (Thermo Fisher Scientific), which targets greater than 1 Mb of genomic sequence corresponding to more than 500 genes recurrently altered in human cancers; total mapped NGS reads for targeted sequencing ranged from 5,069,230-8,497,096 (corresponding to 347-596× coverage across the targeted regions). Prioritized variants and copy number alterations from targeted NGS data were manually curated by an experienced molecular pathologist (A.M.U.) using previously established criteria.60

Aggarwal, et al. Cluster Designation

The unsupervised analysis from Aggarwal, et al. 25 identified five clusters using 119 samples. That study identified 528 genes that were the most differentially expressed between the clusters. Using that gene list, cluster assignments for new samples included in this matched biopsy cohort were determined without replicating the unsupervised analysis. First, the sample batch effect between the samples from the previous study and those from the current study was addressed with exponential normalization on the expression data of all samples—old and new. Exponential normalization is a per-sample operation that fits the expression of all genes to a unit exponential distribution. Next, scikit-learn's k-nearest-neighbor classifier implementation (Pedregosa, F., et al. Scikit-learn: Machine Learning in Python. J Mach Learn Res 12, 2825-2830 (2011)) was used to train a classification model using 118 exponential-normalized samples that had pre-existing cluster assignments. The model used 507 genes from the 528-gene list from Aggarwal, et al. 25 because several genes were not expressed in the previously uncharacterized samples used in this report. The model's accuracy in leave-one-out cross validation was 0.712. The trained model was then used to predict the cluster assignment of previously unclassified, exponential-normalized samples.

Labrecque, et al. Classification

To determine the Labrecque classification, a 26 gene signature used previously to define five phenotypic categories of CRPC 24 was applied: AR-high prostate cancer (ARPC), amphicrine prostate cancer, AR-low prostate cancer (ARLPC), double-negative prostate cancer (DNPC), and neuroendocrine prostate cancer (NEPC) 24. One gene (TARP) was missing from the dataset and was not included. Samples were assigned to the phenotype groups by clustering using Euclidean distance calculated by the dist function and visualization using classical multidimensional scaling (MDS) calculated with the cmdscale function in R using the log2(TPM+1) transformed expression profiles of the remaining 25 genes.

Single-Sample Gene Signature Scores

In this study, several gene signatures collected from public resources, including Zhang Basal gene signature 28, Beltran, et al. NEPC Up gene signature 22, ARG10 signature 27, and Kim, et al. 76 gene AR-repressed signature 29 were used. The signature genes are listed in Table 8. TPM gene expression values were log2(TPM+1) transformed and converted to z-scores by: $z=(x-\mu)/\sigma$, where $\mu$ is the average log2(TPM+1) across all samples of a gene and 6 is the standard deviation of the log2(TPM+1) across all samples of a gene. The signature score of each sample was the average z-score of all genes in each signature.

Development of a Lineage Plasticity Risk Gene Signature

To derive the lineage plasticity risk signature, differential gene expression analysis was performed using DESeq2 as described above by comparing baseline converter vs. non-converter samples. Genes upregulated in converter samples with adjusted P value <0.1 were included (Table 5). Single-sample lineage plasticity risk signature was derived using the single-sample gene set enrichment analysis (ssGSEA) 8 implemented in the GSVA 9 R package.

Assessment of the Lineage Plasticity Signature in Patient-Derived Xenograft Models Baseline gene expression was examined from 10 human prostate adenocarcinoma PDX models 23. Gene expression of the one tumor (LTL331) that undergoes castration-induced lineage plasticity vs. those that do not were compared: LTL310, LTL311, LTL412, LTL-418, LTL313A, LTL313B, LTL313C, LTL313D, and LTL313H. Then, the fold-change-based gene ranking from the comparison was used to assess the enrichment of the lineage plasticity risk signature we identified using gene set enrichment analysis (Subramanian, A., et al. Gene set enrichment analysis: a knowledge-based approach for interpreting genome-wide expression profiles. Proc Natl Acad Sci USA 102, 15545-15550 (2005)).

Survival Analysis

Correlation of the lineage plasticity risk signature with survival time was evaluated in two independent datasets. First, after excluding patients that overlapped with this current study, 17 patients whose tumors had undergone RNA-seq from the prior prospective enza clinical trial with overall survival information were identified 18. Second, samples from the International Dream Team dataset for which overall survival from first line ARSI treatment was available were identified; patients were restricted to those without prior exposure to abiraterone, enza or docetaxel 10. Then, the gene expression of the three datasets, including the samples in the matched biopsy cohort, was merged into one matrix to calculate the enrichment score of each sample consistently. Single-sample lineage plasticity risk score was derived using the single-sample gene set enrichment analysis (ssGSEA) (Barbie, D. A., et al. Systematic RNA interference reveals that oncogenic KRAS-driven cancers require TBK1. Nature 462, 108-112 (2009)) implemented in the GSVA R package (Hanzelmann, S, Castelo, R. & Guinney, J. GSVA: gene set variation analysis for microarray and RNA-seq data. BMC Bioinformatics 14, 7 (2013)). A signature cutoff was defined to separate the baseline converter samples from the non-converter samples from the matched biopsy cohort with the maximum margin as calculated by taking the average of the lowest score in the non-convert group and highest score in the converter group. Finally, this cutoff was used to stratify samples in the two independent datasets into two groups with high and lineage plasticity signature risk scores. The comparison of the survival pattern between the two groups was performed by the Kaplan-Meier method using the Mantel-Cox log-rank test.

SU2C Sample Relabeling

For several samples, aSU2C IDs were relabeled as baseline or progression based upon when the patient was exposed to enzalutamide. DTB_022_PRO and DTB_024_PRO were relabeled DTB_022_BL and DTB_024_BL, respectively, as those biopsies were performed immediately prior to starting enzalutamide treatment. Correspondingly, DTB_022_PRO2 and DTB_024_PRO2 were relabeled DTB_022_PRO and DTB_024_PRO as those biopsies were performed at progression on enzalutamide. DTB_089_PRO2 was relabeled DTB_089_PRO as patient continued enzalutamide until just after PRO2 biopsy.

Results

By examining the Stand Up to Cancer Foundation/Prostate Cancer Foundation West Coast Dream Team (WCDT) prospective cohort, 21 patients with CRPC who underwent a metastatic tumor biopsy prior to enza and a repeat biopsy at the time of progression and whose tumor cells underwent RNA-sequencing after laser capture microdissection were identified. All progression biopsies were performed prior to discontinuing enza, enabling one to identify resistance mechanisms induced by continued enza treatment.

The study design is shown in FIG. 1A. Patient demographic information and prior treatments are shown in Table 2. Bone was the most common site for both pre-treatment and progression biopsies. Eighteen of 21 patients had the same tissue type biopsied at progression. In eight patients, the exact same lesion was biopsied at baseline and progression (FIG. 1B, Table 3). The median time on enza treatment was 226 days. PSA response at 12 weeks and the time between biopsies for each patient are shown in FIG. 1C.

Figure 2:
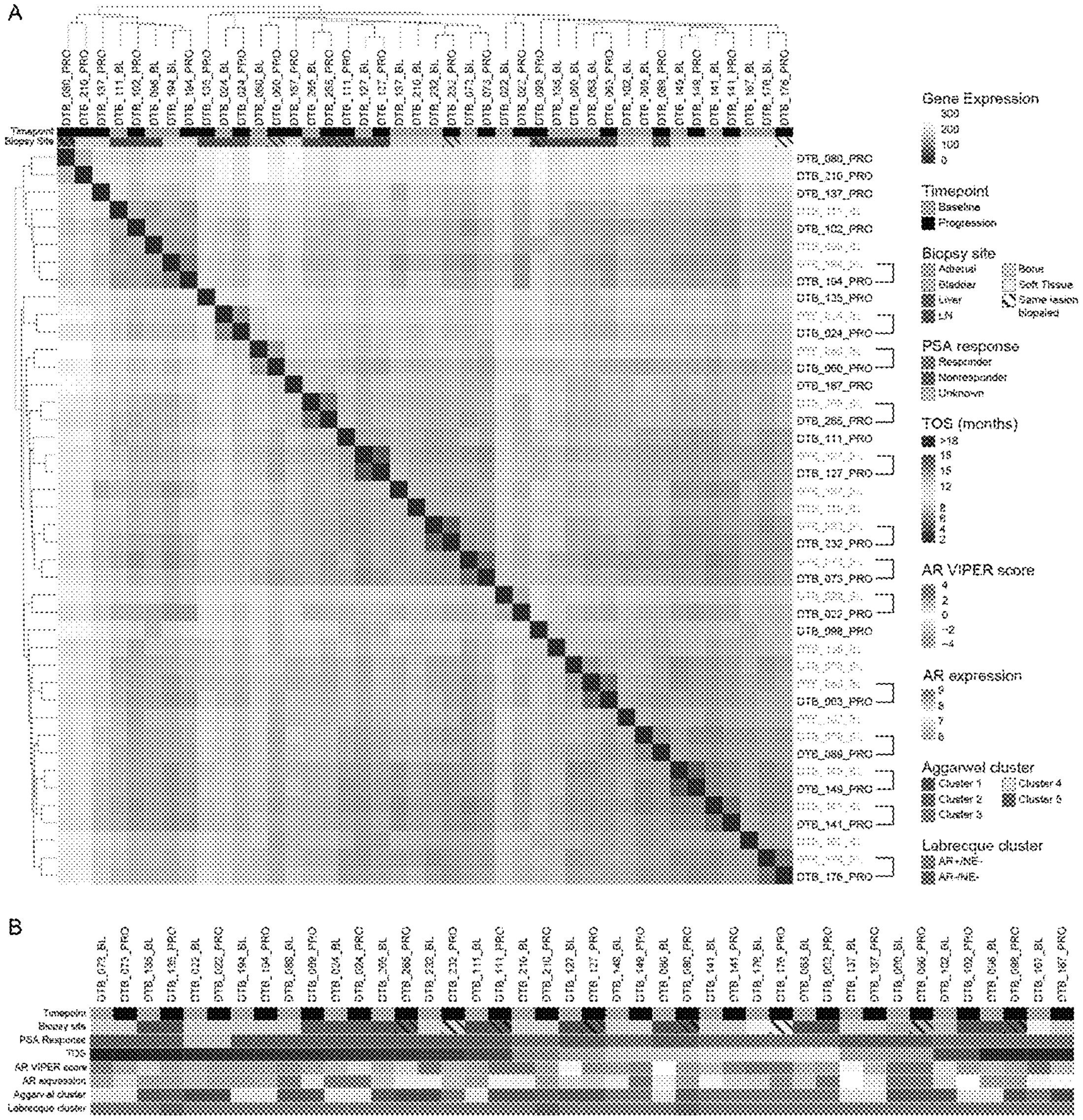
FIG. 2 shows that the effect of enzalutamide on tumor transcriptome is heterogenous across patients. a. Similarity heatmap for all samples clustered by variance-stabilization transformation (vst). b. Clinical and gene expression data for each matched pair ordered on x-axis by time between biopsies.

To understand sample-to-sample differences, unsupervised hierarchical clustering was performed to find the nearest neighbor of 13/21 (62%) baseline samples and their matched progression sample pair (FIG. 2A). Samples did not cluster together based solely on the site of biopsy, indicating laser capture microdissection removed much of the microenvironment from these samples. Furthermore, whether the same lesion was biopsied did not impact how samples clustered.

Figure 5:
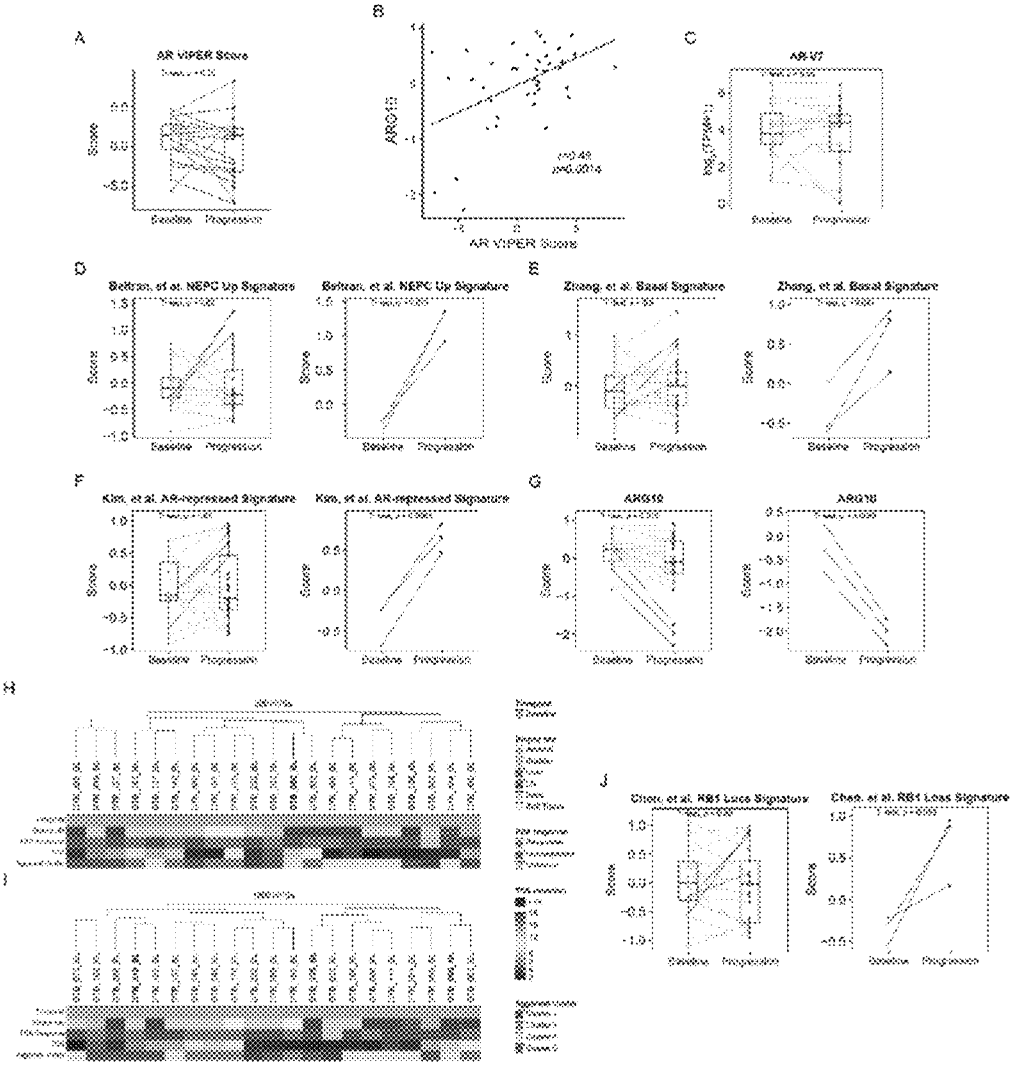
FIG. 5 shows a. AR VIPER Score for each baseline and progression sample. b. ARG10 and VIPER AR score are strongly correlated. c. AR-V7 splice variant expression for each baseline and progression sample. Signature scores were calculated for baseline and progression samples using Beltran, et al. NEPC upregulated genes in d, Zhang, et al. basal genes in e, Kim, et al. AR-repressed lineage plasticity genes in f, and ARG10 genes in g. h. Unsupervised hierarchical clustering of all baseline samples using top 500 differentially expressed genes. i. Unsupervised hierarchical clustering of all baseline samples using top 1000 differentially expressed genes. j. Signature scores were calculated for baseline and progression samples using genes upregulated with RB1 loss described by Chen, et al.

Measurements of interest were examined in all the matched samples (FIG. 2B). To estimate AR transcriptional activity, Virtual Inference of Protein-activity by Enriched Regulon (VIPER) master regulator analysis was used 26. Nine (43%) patients did not have a marked difference in inferred AR activity. Nine (43%) patients had decreased AR activity, and three (14%) patients had increased AR activity at progression (FIG. 5A). A second method to measure AR activity—the ARG10 signature was used 27. ARG10 strongly correlated with the VIPER results (FIG. 5B). Though AR-V7 expression increased in several samples at progression, the difference in expression using the entire 21-patient cohort was not statistically significant (FIG. 5C).

Five clusters of CRPC tumors have been identified by RNA-sequencing analysis 25. Cluster 2 was enriched for tumors with loss of AR activity, increased E2F1 activity, and contained a preponderance of tumors that had lost AR expression 25, consistent with lineage plasticity. A subset of cluster 2 tumor samples was labeled NEPC based upon their morphologic appearance resembling small cell prostate cancer 25, though many of these tumor samples did not express canonical NEPC markers such as chromogranin A (CHGA) or synaptophysin (SYP) 25.

In examining the RNA-sequencing results from the baseline tumors, four of the five Aggarwal clusters were represented (clusters 1, 3, 4, and 5) in at least one sample, while no baseline sample harbored a cluster 2 program. The Labrecque transcription-based classifier that was developed on rapid autopsy CRPC samples was used to identify five subsets of prostate cancer: AR-driven prostate cancer (ARPC), amphicrine prostate cancer with neuroendocrine gene expression concomitant with AR signaling, AR-activity low prostate cancer, DNPC, and NEPC 24. The Labrecque classifier designated all the baseline samples in our cohort as ARPC.

To determine if any of the progression tumors in the cohort underwent lineage plasticity after enza, the Aggarwal cluster and Labrecque classifier designation were determined. Twelve of 21 matched pairs did not change their Aggarwal cluster designation. However, three of the 21 progression tumors (hereafter referred to as converters) had gene expression profiles consistent with cluster 2, supporting enza-induced conversion to an alternate lineage. The Labrecque classifier was also examined on the progression samples. The three converter samples designated as Aggarwal cluster 2 at progression were most consistent with DNPC by the Labrecque classifier, corroborating lineage plasticity in these tumors (FIG. 2B).

Additional gene signatures linked previously to lineage plasticity in progression vs. baseline biopsies were examined Comparing samples from the three converter patients, signature scores for genes upregulated in NEPC tumors described by Beltran, et al. 22 were increased (FIG. 5D). A previously described basal stemness signature 28 was also activated in these three progression samples (FIG. 5E). A 76 gene AR-repressed gene signature that was activated in a CRPC cell line that undergoes enza-induced lineage plasticity 29 was also increased in the progression samples from the three converters (FIG. 5F). Finally, predicted AR activity was significantly decreased in the progression samples from the converters by both VIPER and ARG10 signatures (FIG. 5A, 1G). In examining pre- and post-treatment samples using the entire 21-patient cohort, none of these signatures was significantly changed, demonstrating that activation of these lineage plasticity signatures was not a generalized effect of enza treatment. Altogether, these results suggest that enza-induced lineage plasticity and conversion to an AR-independent program occurs in a subset of tumors (3/21 or 14%), similar to the frequency of cluster 2 tumors (10%) described by Aggarwal previously[25].

Notably, the baseline tumors from the three converter patients did not fall into the same Aggarwal cluster (cluster 4 for sample 80 and cluster 5 for samples 135, 210). The baseline tumors from these three patients did not cluster together using unsupervised clustering (FIG. 5H, 1I). These data indicate that there may be different starting points to lineage plasticity with enza treatment.

Figure 3:
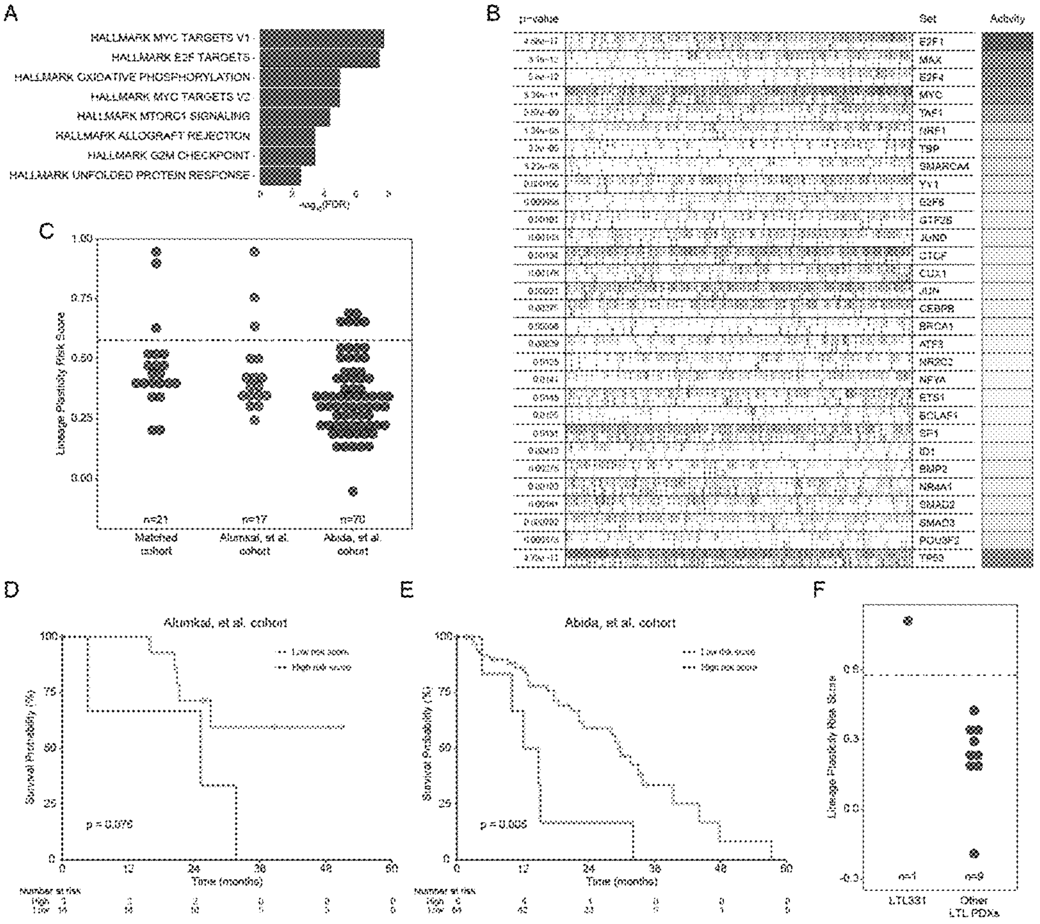
FIG. 3 shows that pathway and master regulator analysis implicate E2F1 in lineage plasticity risk, and a signature of lineage plasticity risk identifies tumors with poor outcomes after androgen receptor signaling inhibitor treatment. a. Hallmark pathway analysis of activated pathways in baseline samples for the three patients whose tumors converted (underwent lineage plasticity) vs. those patients whose tumors did not upon progression. b. Master regulator analysis identifies top activated and deactivated transcription factors between converters and non-converters using the baseline tumor samples. c. Dot plot showing lineage plasticity signature score for patients in indicated cohorts. d,e. Kaplan-Meier survival curves for patients in the Alumkal, et al. cohort (d) and Abida, et al. cohort (e) stratified by high or low lineage plasticity risk score. f. Dot plot showing lineage plasticity signature score for all castration naïve adenocarcinoma PDX models described by Lin, et al.[23]

To identify genes linked with risk of lineage plasticity after enza, the differentially expressed genes between the three baseline samples from converters vs. the 18 non-converters were examined Pathway analysis implicated activation of MYC targets, E2F targets, and allograft rejection in baseline tumors from converters (FIG. 3A). There were no significantly downregulated pathways in baseline tumors from converters. To identify differentially activated transcription factors, master regulator analysis was performed. E2F1 was the top transcription factor predicted to be activated in the baseline tumors from converters (FIG. 3B, Table 4). Additionally, it was found that there was an upward trend in a previously described RB1 loss signature 31 in the progression samples from converters, further supporting that E2F1 activation contributes to the lineage switch (FIG. 5J). Other highly activated transcription factors in the baseline samples from converters include MYC family members and E2F4. Conversely, TP53—whose loss has been linked to lineage plasticity[28,32-33]—was predicted to be the most deactivated transcription factor (FIG. 3B).

Figure 6:
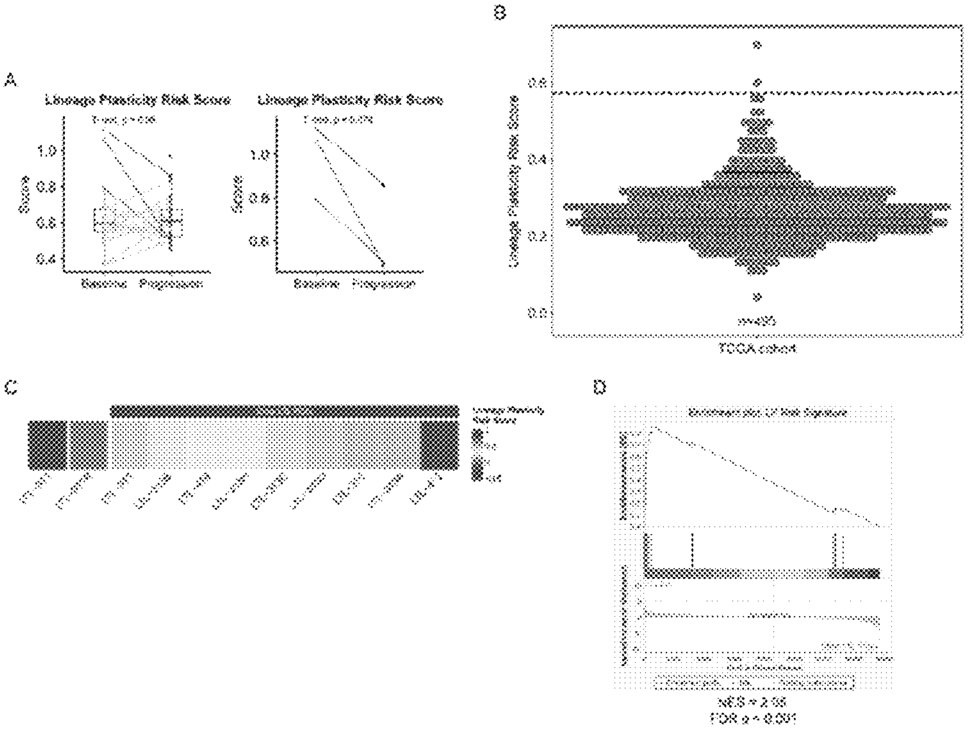
FIG. 6 shows a. lineage plasticity risk scores calculated for baseline vs. progression samples. b. Dotplot showing lineage plasticity risk signature score for patients described in prostate cancer TCGA15. c. Heatmap showing lineage plasticity risk score in LTL331, other hormone-naïve LTL PDXs, and LTL331R described by Lin, et al. d. Gene set enrichment plot for 14 gene lineage plasticity risk signature in LTL331 vs. other nine hormone-naïve LTL PDXs described in Lin, et al.
Figure 7:
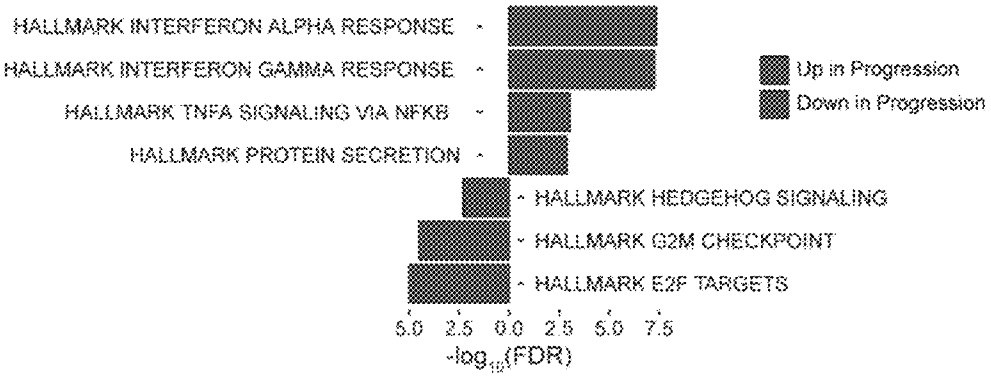
FIG. 7 shows Hallmark pathway analysis demonstrating the top up- or downregulated pathways in progression vs. baseline samples for the 18 patients whose tumors did not convert.

Next, genes that were significantly upregulated in the baseline tumors from converters vs. non-converters were identified. A 14-gene signature highly activated in the three baseline tumors from converters was identified (Table 5). Genes in this signature include those linked to: the Wnt pathway (RNF43 32 and TRABD2A 33), the spliceosome (SNRPF 34), and the electron transport chain (NDUFA12 35 and ATPSB 36). This signature trended downwards in the progression vs. baseline biopsies from the three converters (FIG. 6). These results indicate that this signature is not simply identifying tumor cells that have already undergone lineage plasticity prior to enza treatment. Rather, these genes may be markers of a transition state in cells susceptible to lineage plasticity.

Dividing the baseline samples between converters and non-converters, a cut off for this 14-gene lineage plasticity risk signature that separated the groups was defined (FIG. 3C). Additional cohorts with matched biopsies before and after enza with lineage plasticity information are lacking. However, it was hypothesized that patients whose baseline tumors had high scores for this lineage plasticity risk signature would have worse outcomes. Survival data from the time of ARSI treatment were available for several CRPC cohorts whose tumors had undergone RNA-sequencing—the International Dream Team dataset 10 and a prior prospective enza clinical trial led by our group 18. Because a subset of the patients in that latter enza clinical trial overlapped with the patients in this current report, patients from that clinical trial not represented here were analyzed. Using the pre-defined 14-gene signature score cut-off from the matched biopsy cohort, it was determined that high scores were associated with worse overall survival from the time of ARSI treatment in both independent datasets ($p=0.076$, $p=0.006$; FIG. 3D, E). Thus, high expression of the 14-gene lineage plasticity risk signature is linked to poor patient outcomes after ARSI treatment in CRPC. To determine if the lineage plasticity risk signature was activated in primary tumors, the TCGA dataset 39 was examined Importantly, only two of 495 patients had high risk scores (FIG. 6B). The lower frequency in primary tumors vs. CRPC cohorts suggests that activation of this lineage plasticity risk program may be induced by castration.

Validation datasets with matched biopsies before and after ARSI treatment that include information on lineage at time of progression are lacking. However, the impact of surgical castration on adenocarcinoma patient-derived xenografts (PDX) has been determined 23. Nine PDXs did not undergo castration-induced lineage plasticity, while one PDX—LTL331—does and converts to a resistant version called LTL331R 23. The patient from whom the LTL331 PDX is derived had evidence of lineage plasticity in his tumor when it became castration-resistant, demonstrating this model's fidelity 23,37. The lineage plasticity risk signature was highly activated in LTL331 vs. the other hormone naïve PDXs that do not undergo castration-induced lineage plasticity (FIG. 3F, 6C,D). Indeed, LTL331 was the only PDX whose lineage plasticity risk score was greater than the cut-off defined in the matched biopsy cohort (FIG. 3F). Prior work demonstrates that the exome of LTL331 is strikingly similar to its castration-induced lineage plasticity derivative, strongly suggesting that transdifferentiation—rather than clonal selection—may explain conversion in this tumor 23. Finally, the lineage plasticity risk score decreased in LTL331R vs. LTL331 (FIG. 6C), similar to the pattern observed in the progression vs. baseline samples from converters in our matched biopsy cohort (FIG. 6A).

Figure 4:
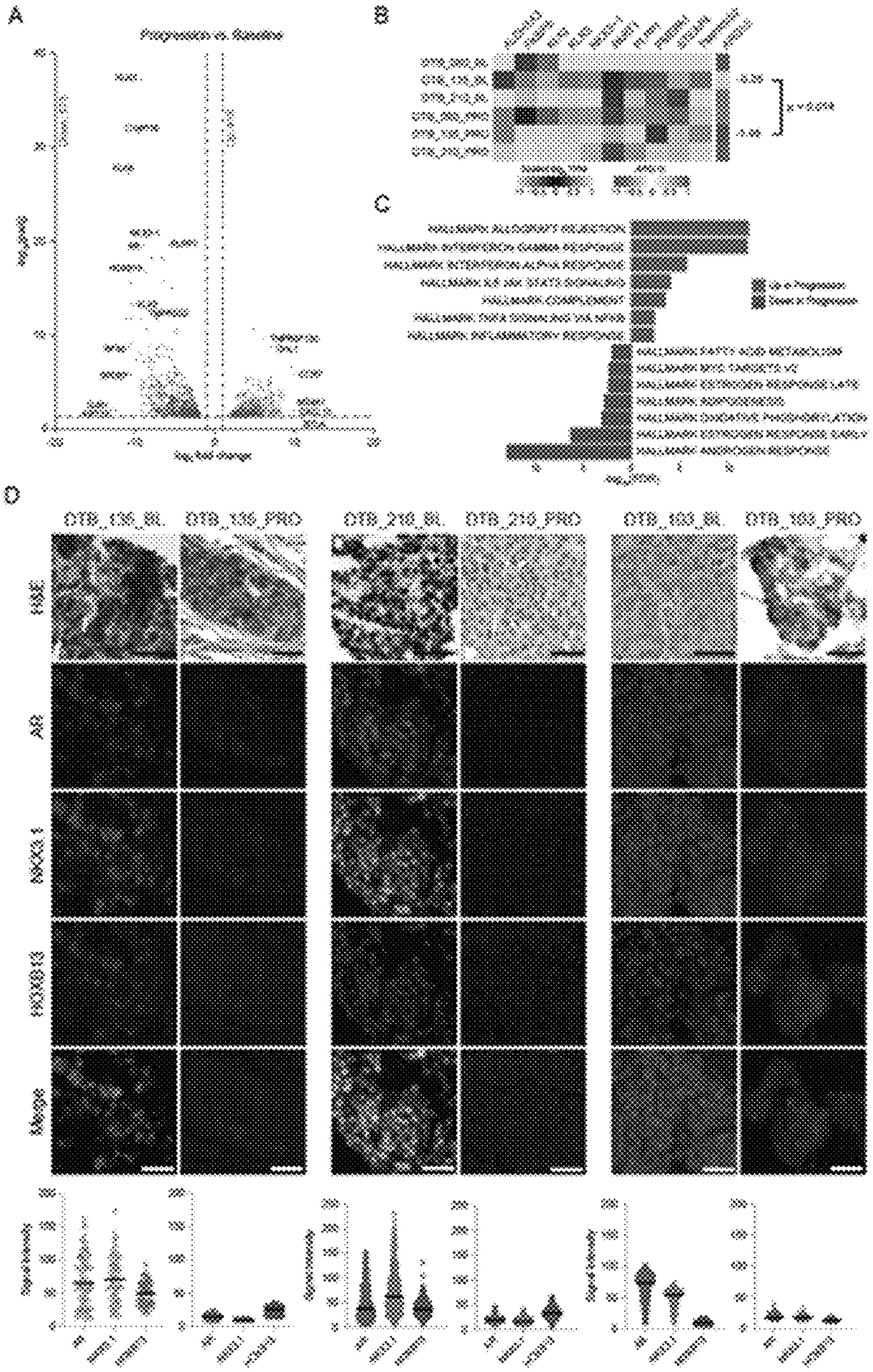
FIG. 4 gene expression profiling and multiplex immunofluorescence that identify gene expression changes in tumors undergoing enzalutamide-induced lineage plasticity. a. Volcano plot showing top up and down regulated genes in progression samples vs. baseline samples for the three patients whose tumors converted. b. ARG10 gene signature heatmap for three converters at baseline and progression. The left half shows the expression levels of individual genes in the ARG10 signature, and the right half shows the ARG10 signature score. p-value shown is for a paired t-test between baseline and progression ARG10 scores (n=3 pairs). c. Hallmark pathway analysis shows the top up or down regulated pathways in progression vs. baseline samples for the three patients whose tumors converted d. Multiplex immunofluorescence for AR, NKX3.1, and HOXB13 expression between baseline vs. progression samples for patient 135, 210, and an additional West Coast Dream Team patient (patient 103) whose tumor converted. Scale bar represents 50 μm.

Next, changes induced by enza between the baseline and progression samples from the three converters were investigated. The top differentially expressed genes are shown in FIG. 4A. The AR, AR target genes (KLK2, KLK3, and TMPRSS2), and the AR coactivator HOXB13 had markedly decreased expression (FIG. 4A, Table 6). In keeping with this, progression biopsies from converters had significantly reduced expression of AR target genes from the ARG10 gene signature 27 (FIG. 4B). Genes from the Beltran NEPC Upregulated signature were increased in progression samples from converters (FIG. 5B). It is worth noting that this signature contains both canonical NEPC genes and genes not explicitly associated with acquisition of neuroendocrine features that are AR-repressed. Specifically, examining canonical NEPC markers such as SYP, CHGA, and NCAM1, it was found that these genes were not highly upregulated at progression (Table 7). Other genes linked to NEPC (SYT11, CIITA, and ETVS) 22 or those normally repressed by the AR (CDCA7L, FRMD3, IKZF3, and TNFAIP2) 29 were more highly-expressed in the progression biopsies, indicating that these three converter tumors may be farther along the lineage plasticity spectrum than the previously described non-neuroendocrine DNPC subtype but not as far along as de novo NEPC or NEPC found at rapid autopsy by Labrecque, et al. 24 that harbor a more complete neuroendocrine program.

Pathway analysis between baseline and progression samples from the three converters demonstrated enrichment in several pathways, including: allograft rejection, interferon gamma response, interferon alpha response, and IL6/JAK/STAT signaling (FIG. 4C). Conversely, androgen and estrogen response—both linked to luminal differentiation—were the most downregulated, confirming loss of AR-dependence. Differences in gene expression between baseline and progression samples from the 18 patients whose tumors did not undergo lineage plasticity were examined. Several of the pathways activated in the converter tumors were also activated in the non-converters—namely, interferon alpha response, interferon gamma response, and TNF-α signaling (FIG. 9). Uniquely upregulated pathways in the converters include: allograft rejection, IL6-JAK-STAT3 signaling, inflammatory response, and complement. Uniquely downregulated pathways in the progression samples from non-converters included: E2F targets, G2M checkpoint, and hedgehog signaling. The only uniquely upregulated pathway in non-converters was protein secretion while uniquely downregulated pathways included hedgehog signaling, G2M checkpoint and E2F targets.

Figure 8:
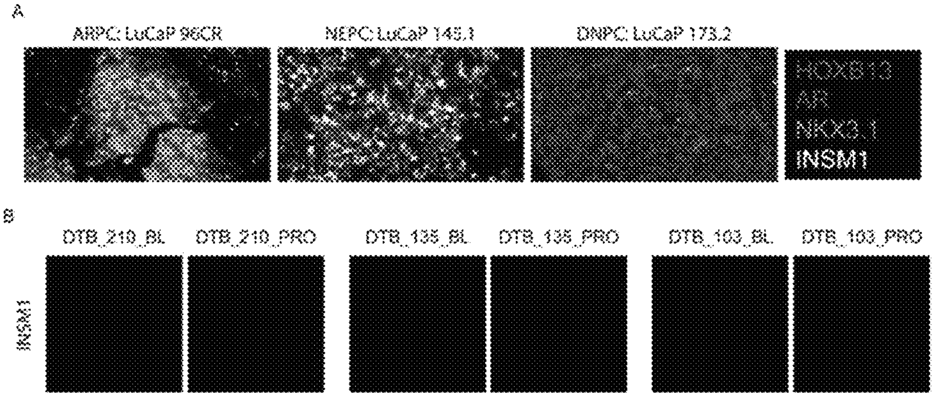
FIG. 8 shows a. Panels show expression of AR, NKX3.1, INSM1, and HOXB13 in ARPC LuCaP 96CR PDX tumor, NEPC LuCaP 145.1 PDX tumor, and DNPC LuCaP 173.2 PDX tumor. AR and NKX3.1 were only expressed in LuCaP 96CR. INSM1 was only expressed in LuCaP 145.1, while HOXB13 was expressed in both LuCaP 96CR and LuCaP 173.2. b. Absent INSM1 expression in all three matched converter samples examined.

To understand the architecture of the tumors from the three converters, multiplex immunofluorescence (IF) was used with three luminal lineage markers (AR, NKX3.1, and HOXB13)—all downregulated at the mRNA level by RNA-sequencing (FIG. 4A)—and the NEPC marker INSM1 38. LuCaP PDX samples were used as positive and negative controls (FIG. 8B). Matched tissue samples for multiplex IF were available for subjects 135 and 210 but not for subject 80. One additional WCDT subject (103) with matched biopsies whose tumor underwent rapid clinical progression after enza treatment in the setting of a falling serum PSA—a clinical marker of AR-independence was identified. Matched RNA-sequencing was not available for this subject, but his tumor exhibited evidence of lineage plasticity (FIG. 4D). Representative staining images and quantitation of these markers are shown in FIG. 4D. There was a spectrum of AR, NKX3.1, and HOXB13 expression in baseline samples with some cells expressing low levels of each marker, while other cells expressed higher levels. However, at progression, there was a convergence towards population-wide loss of AR, NKX3.1, and HOXB13 in each sample. INSM1 upregulation was not identified in any of the baseline or progression tumors (FIG. 8C). These results match RNA-sequencing that failed to demonstrate upregulation of other canonical NEPC markers (Table 7) and that characterized the three converter samples as DNPC by the Labrecque classifier, rather than NEPC (FIG. 2B).

Finally, to determine if the progression samples from converters represented distinct clones with unique genetic alterations vs. baseline, DNA mutation and copy number analysis were performed. For subjects 80 and 103, the same tumor lesion was biopsied at baseline and progression. DNA-sequencing of these biopsies showed identical DNA mutations. For subjects 135 and 210, matched metastatic biopsy DNA-sequencing was unavailable. However, cell-free DNA was available. DNA-sequencing of cell-free DNA samples showed that mutations and copy number alterations were conserved between baseline and progression samples (Table 1).

Loss of the tumor suppressor genes TP53, RB1, and PTEN has been linked to lineage plasticity risk in pre-clinical models[32,33]. However, it is not known if the presence of these genomic abnormalities in patient tumors is associated with risk of lineage plasticity to DNPC. One of the three converter patients (subject 80) was found to have an inactivating PTEN mutation and a second patient (subject 103) had RB1 loss, but none were found to have compound TP53/RB1/PTEN loss. When available, TP53/RB1/PTEN status for tumors from the Abida, et al.[10] and Alumkal, et al.[18] cohorts that had high lineage plasticity risk scores was examined. Of the seven high lineage plasticity risk score tumors examined from these two validation cohorts, only two tumors had loss of two or more of the genes TP53, RB1, and PTEN (Table 9). DNA-sequencing of matched metastatic biopsies for the cohort as a whole is shown in Table 10.

TABLE 1

DNA sequencing of matched samples from converters demonstrates conserved alterations.

| Patient ID | Mutation | Copy number gain/loss |
|---|---|---|
| DTB_80_BL | PTEN | |
| DTB_80_Pro | PTEN | |
| DTB_103_BL | RB1, FGFR3, NOTCH1 | |
| DTB_103_Pro | RB1, FGFR3, NOTCH1 | |
| DTB_135_BL | SPEN, FAT1 | AR amplification, MYC amplification |
| DTB_135_Pro | SPEN, FAT1, CTNNB1 (subclonal) | AR amplification, MYC amplification |
| DTB_210_BL | APC, SPOP, KMT2C | |
| DTB_210_Pro | APC, SPOP, KMT2C | |

TABLE 2

Patient demographics and clinical information summary

| Patients | n = 21 |
|---|---|
| Median age at time of enrollment (SD) | 71 (58-88) |
| Gleason score at diagnosis | |
| ≥8 | 16 |
| <8 | 5 |
| ECOG performance status (%) | |
| 0 | 10 |
| 1 | 11 |
| Metastatic site biopsied baseline (progression) | |
| Bone | 9 (9) |
| Lymph node | 7 (8) |
| Pelvic soft tissue | 2 (1) |
| Bladder wall | 1 (0) |
| Liver | 1 (2) |
| Adrenal | 1 (1) |
| Same lesion biopsied | 8 |
| Visceral metastatic disease at time of biopsy | 5 |
| Prior treatment | |
| Abiraterone | 7 |
| ADT | 21 |
| Bicalutamide | 8 |
| Cabazitaxel | 1 |
| Docetaxel | 3 |
| Sip-T | 1 |
| Median PSA at enrollment (SD) | 57 (200) |
| 50% PSA response to enzalutamide | 7 |
| Median time on enzalutamide, days (SD) | 261 (315) |

TABLE 3

Patient and biopsy information

| Sample_ID | Baseline biopsy tissue | Progression tissue | Same site biopsied | Time Between Biopsies | PSA at baseline | PSA Change at 12 weeks | Prior treatment |
|---|---|---|---|---|---|---|---|
| DTB_022 | Bone | Bone | No | 85 | 7.28 | N/A | ADT, abiraterone |
| DTB_024 | Liver | Liver | No | 99 | 48.92 | 75.05 | ADT, abiraterone, docetaxel |

TABLE 3-continued

| Patient and biopsy information | | | | | | | |
|---|---|---|---|---|---|---|---|
| Sample_ID | Baseline biopsy tissue | Progression tissue | Same site biopsied | Time Between Biopsies | PSA at baseline | PSA Change at 12 weeks | Prior treatment |
| DTB_060 | Adrenal | Adrenal | Yes | 449 | 102.45 | −20.41 | ADT |
| DTB_063 | LN | LN | No | 368 | 20.9 | −74.64 | ADT |
| DTB_073 | Bone | Bone | No | 54 | 57.67 | 156.81 | ADT, Abiraterone |
| DTB_080 | LN | LN | Yes | 266 | 14.92 | −28.48 | ADT |
| DTB_089 | Bone | Liver | No | 91 | 14.27 | 181.18 | ADT, Abiraterone |
| DTB_098 | LN | LN | Yes | 615 | 148.39 | −83.74 | ADT |
| DTB_102 | Bladder | LN | No | 533 | 1210.48 | −93.02 | ADT, abiraterone, docetaxel, cabazitaxel |
| DTB_111 | LN | LN | Yes | 134 | 35.02 | 113.99 | ADT, Abiraterone |
| DTB_127 | LN | LN | Yes | 226 | 228 | 169.29 | ADT, Abiraterone |
| DTB_135 | LN | LN | No | 73 | 9.19 | 164.26 | ADT, bicalutamide |
| DTB_137 | Bone | Bone | No | 441 | 539.62 | −10.85 | ADT, bicalutamide |
| DTB_141 | Bone | Bone | No | 285 | 140.07 | −81.04 | ADT, bicalutamide |
| DTB_149 | Bone | Bone | No | 262 | 16.45 | −80.29 | ADT, bicalutamide |
| DTB_167 | Soft tissue | Bone | No | 827 | 136.64 | −88.38 | ADT, bicalutamide, sipuleucel-T |
| DTB_176 | Soft tissue | Soft tissue | Yes | 291 | 3.57 | −64.76 | ADT, bicalutamide |
| DTB_194 | Bone | Bone | No | 88 | 103.55 | 100.36 | ADT, bicalutamide |
| DTB_210 | Bone | Bone | No | 200 | 70.45 | −83.36 | ADT |
| DTB_232 | Bone | Bone | Yes | 114 | 5.31 | −0.55 | ADT, docetaxel |
| DTB_265 | LN | LN | Yes | 105 | 42.93 | 5.84 | ADT, bicalutamide |

TABLE 4

| Converter vs. non-converter baseline Master Regulator analysis | | | | |
|---|---|---|---|---|
| | Regulon | Size | NES | p.value |
| ABL1 | ABL1 | 29 | 0.051236 | 0.959138 |
| ACTB | ACTB | 22 | −1.01068 | 0.312171 |
| AHR | AHR | 195 | −1.74628 | 0.080762 |
| AIF1L | AIF1L | 30 | −0.03049 | 0.97568 |
| ANG | ANG | 16 | −0.20733 | 0.83575 |
| APOB | APOB | 13 | 0.23179 | 0.816701 |
| AR | AR | 504 | −2.00987 | 0.044445 |
| ARID3A | ARID3A | 15 | 1.15268 | 0.249042 |
| ARNT | ARNT | 20 | 1.271309 | 0.203619 |
| ARVCF | ARVCF | 24 | −0.92051 | 0.357304 |
| ASCL1 | ASCL1 | 25 | −0.90166 | 0.367238 |
| ATF1 | ATF1 | 60 | −0.67157 | 0.501858 |
| ATF2 | ATF2 | 111 | −2.28452 | 0.022341 |
| ATF3 | ATF3 | 256 | 2.636052 | 0.008388 |
| ATF4 | ATF4 | 77 | 1.324082 | 0.185476 |
| ATF6 | ATF6 | 48 | 0.596372 | 0.550927 |
| ATOH1 | ATOH1 | 11 | −0.79886 | 0.42437 |
| BACH1 | BACH1 | 19 | −0.64787 | 0.517068 |
| BARX2 | BARX2 | 16 | −1.15849 | 0.246664 |
| BATF | BATF | 117 | 1.915968 | 0.055369 |
| BCL11A | BCL11A | 65 | −0.45344 | 0.650232 |
| BCL3 | BCL3 | 187 | 2.151217 | 0.031459 |
| BCL6 | BCL6 | 77 | −0.44056 | 0.659529 |
| BCLAF1 | BCLAF1 | 139 | 2.42129 | 0.015466 |
| BCR | BCR | 47 | −0.28628 | 0.774662 |
| BDP1 | BDP1 | 68 | −0.69727 | 0.485632 |
| BHLHE40 | BHLHE40 | 33 | −1.88141 | 0.059916 |
| BMP2 | BMP2 | 269 | −2.994 | 0.002753 |

TABLE 4-continued

| Converter vs. non-converter baseline Master Regulator analysis | | | | |
|---|---|---|---|---|
| | Regulon | Size | NES | p.value |
| BRCA1 | BRCA1 | 168 | 2.87972 | 0.00398 |
| BRF1 | BRF1 | 25 | −0.26372 | 0.791995 |
| BRF2 | BRF2 | 30 | −0.24797 | 0.804161 |
| CBX5 | CBX5 | 16 | −0.13761 | 0.890549 |
| CCDC116 | CCDC116 | 47 | 0.152711 | 0.878626 |
| CCL20 | CCL20 | 15 | 0.481348 | 0.630269 |
| CCNT2 | CCNT2 | 78 | 0.109371 | 0.912908 |
| CDC45 | CDC45 | 18 | −0.74948 | 0.453568 |
| CEBPB | CEBPB | 429 | 2.898243 | 0.003753 |
| CEBPZ | CEBPZ | 73 | −0.56453 | 0.572395 |
| CHD2 | CHD2 | 210 | 2.415137 | 0.015729 |
| CIC | CIC | 14 | −1.52926 | 0.1262 |
| CLIC1 | CLIC1 | 20 | −0.44992 | 0.652767 |
| CLOCK | CLOCK | 29 | 1.260735 | 0.207404 |
| COMT | COMT | 19 | −0.71566 | 0.474203 |
| CREB1 | CREB1 | 127 | −0.53051 | 0.595761 |
| CREM | CREM | 48 | 0.069052 | 0.944948 |
| CRKL | CRKL | 36 | −0.32866 | 0.742414 |
| CSNK2B | CSNK2B | 15 | −1.19408 | 0.232447 |
| CTBP2 | CTBP2 | 110 | −2.37744 | 0.017433 |
| CTCF | CTCF | 1030 | 3.206967 | 0.001341 |
| CUX1 | CUX1 | 405 | 3.125283 | 0.001776 |
| DACH1 | DACH1 | 152 | 2.282266 | 0.022474 |
| DBP | DBP | 62 | 1.594974 | 0.110718 |
| DCAF11 | DCAF11 | 21 | −0.62929 | 0.529162 |
| DDAH2 | DDAH2 | 15 | 0.361102 | 0.718024 |
| DDIT3 | DDIT3 | 134 | 0.499877 | 0.617162 |
| DGCR8 | DGCR8 | 26 | −0.23777 | 0.812056 |

TABLE 4-continued

Converter vs. non-converter baseline Master Regulator analysis

| | Regulon | Size | NES | p.value |
|---|---|---|---|---|
| DHRS2 | DHRS2 | 27 | −0.52634 | 0.598652 |
| DLX2 | DLX2 | 36 | −1.9245 | 0.054292 |
| DLX5 | DLX5 | 23 | −0.33429 | 0.738162 |
| E2F1 | E2F1 | 740 | 8.39697 | 4.58E−17 |
| E2F2 | E2F2 | 24 | 1.350676 | 0.176799 |
| E2F3 | E2F3 | 33 | −0.65908 | 0.509844 |
| E2F4 | E2F4 | 260 | 6.889355 | 5.60E−12 |
| E2F6 | E2F6 | 260 | 3.302534 | 0.000958 |
| EBF1 | EBF1 | 184 | −0.85838 | 0.390681 |
| EEF1A1 | EEF1A1 | 15 | −1.15332 | 0.248781 |
| EGR1 | EGR1 | 540 | −1.50333 | 0.132754 |
| EGR2 | EGR2 | 58 | −0.64473 | 0.519102 |
| EGR3 | EGR3 | 11 | −0.43829 | 0.661177 |
| ELF1 | ELF1 | 379 | −1.2287 | 0.219183 |
| ELF3 | ELF3 | 36 | 0.866801 | 0.386051 |
| ELK1 | ELK1 | 177 | 1.107087 | 0.268256 |
| ELK3 | ELK3 | 23 | −1.03345 | 0.301394 |
| ELK4 | ELK4 | 93 | −0.6164 | 0.537629 |
| EN1 | EN1 | 16 | −0.931 | 0.351853 |
| EP300 | EP300 | 427 | −1.49352 | 0.1353 |
| EPAS1 | EPAS1 | 71 | −0.74583 | 0.455769 |
| ERF | ERF | 23 | −0.18083 | 0.856505 |
| ERG | ERG | 45 | −0.61526 | 0.538381 |
| ESR1 | ESR1 | 389 | −2.25367 | 0.024217 |
| ESR2 | ESR2 | 90 | −0.89841 | 0.36897 |
| ESRRA | ESRRA | 69 | 0.088802 | 0.929239 |
| ETS1 | ETS1 | 538 | 2.444806 | 0.014493 |
| ETS2 | ETS2 | 60 | −1.10991 | 0.267037 |
| ETV4 | ETV4 | 33 | 0.985929 | 0.324168 |
| ETV6 | ETV6 | 61 | 0.012768 | 0.989813 |
| EVX1 | EVX1 | 11 | −1.35387 | 0.175777 |
| EZH2 | EZH2 | 54 | 1.776698 | 0.075618 |
| FAM78A | FAM78A | 17 | −0.16198 | 0.871318 |
| FANK1 | FANK1 | 31 | −0.1858 | 0.852601 |
| FBXO31 | FBXO31 | 17 | −1.09211 | 0.274787 |
| FIBCD1 | FIBCD1 | 20 | −0.36686 | 0.713722 |
| FLI1 | FLI1 | 64 | −2.14641 | 0.03184 |
| FOS | FOS | 574 | −1.79691 | 0.072349 |
| FOSB | FOSB | 24 | 0.004458 | 0.996443 |
| FOSL1 | FOSL1 | 120 | 0.130066 | 0.896514 |
| FOSL2 | FOSL2 | 85 | 1.365824 | 0.171994 |
| FOXA1 | FOXA1 | 383 | −1.09373 | 0.274075 |
| FOXA2 | FOXA2 | 213 | 1.892128 | 0.058474 |
| FOXC1 | FOXC1 | 29 | −1.81002 | 0.070292 |
| FOXC2 | FOXC2 | 32 | −0.90415 | 0.365917 |
| FOXL2 | FOXL2 | 21 | −1.18545 | 0.235839 |
| FOXM1 | FOXM1 | 82 | 2.675307 | 0.007466 |
| FOXN1 | FOXN1 | 33 | −0.97553 | 0.329296 |
| FOXO1 | FOXO1 | 142 | −2.32375 | 0.020139 |
| FOXO3 | FOXO3 | 106 | −1.0564 | 0.290786 |
| FOXO4 | FOXO4 | 26 | 0.560582 | 0.575083 |
| FOXP3 | FOXP3 | 85 | 0.971092 | 0.331502 |
| GABPA | GABPA | 366 | 2.163614 | 0.030494 |
| GATA1 | GATA1 | 280 | 0.462909 | 0.64343 |
| GATA2 | GATA2 | 506 | 1.542317 | 0.122997 |
| GATA3 | GATA3 | 511 | −0.55035 | 0.582077 |
| GATA4 | GATA4 | 70 | −1.49867 | 0.133958 |
| GATA6 | GATA6 | 40 | −0.45295 | 0.650588 |
| GFI1 | GFI1 | 21 | 1.522495 | 0.127885 |
| GLI1 | GLI1 | 109 | −1.6911 | 0.090817 |
| GLI2 | GLI2 | 73 | −0.93476 | 0.34991 |
| GLI3 | GLI3 | 48 | −1.20849 | 0.22686 |
| GMPR2 | GMPR2 | 14 | 0.516862 | 0.605253 |
| GNAZ | GNAZ | 16 | −0.51571 | 0.606054 |
| GNB1L | GNB1L | 16 | −1.46036 | 0.144191 |
| GP1BB | GP1BB | 22 | −0.18902 | 0.850079 |
| GTF2B | GTF2B | 231 | 3.288553 | 0.001007 |
| GTF2F1 | GTF2F1 | 76 | 2.911749 | 0.003594 |
| HBP1 | HBP1 | 32 | 0.666748 | 0.504933 |
| HDAC2 | HDAC2 | 89 | 0.702261 | 0.482516 |
| HES1 | HES1 | 70 | 0.4195 | 0.674851 |
| HESX1 | HESX1 | 11 | 0.48202 | 0.629792 |
| HEY1 | HEY1 | 18 | −0.88366 | 0.37688 |
| HHEX | HHEX | 14 | −0.20373 | 0.838562 |
| HIF1A | HIF1A | 261 | −1.22063 | 0.222228 |
| HIF3A | HIF3A | 11 | −0.61827 | 0.5364 |

TABLE 4-continued

Converter vs. non-converter baseline Master Regulator analysis

| | Regulon | Size | NES | p.value |
|---|---|---|---|---|
| HIRA | HIRA | 19 | 0.89105 | 0.372902 |
| HIST1H2AB | HIST1H2AB | 16 | 0.839262 | 0.401322 |
| HIST1H2AD | HIST1H2AD | 18 | 0.032375 | 0.974173 |
| HIST1H2AG | HIST1H2AG | 18 | −0.5441 | 0.586373 |
| HIST1H2AH | HIST1H2AH | 14 | −0.99929 | 0.317654 |
| HIST1H2BD | HIST1H2BD | 17 | −1.04682 | 0.295181 |
| HIST1H2BF | HIST1H2BF | 17 | −0.43296 | 0.665044 |
| HIST1H2BJ | HIST1H2BJ | 18 | −0.86077 | 0.389362 |
| HIST1H3B | HIST1H3B | 16 | −0.37424 | 0.708223 |
| HIST1H3D | HIST1H3D | 18 | −0.26053 | 0.794458 |
| HIST1H4B | HIST1H4B | 17 | 0.253817 | 0.799637 |
| HIST1H4I | HIST1H4I | 19 | 0.385611 | 0.699785 |
| HLX | HLX | 14 | −0.95844 | 0.337843 |
| HMGA1 | HMGA1 | 52 | 0.141333 | 0.887607 |
| HMGN3 | HMGN3 | 55 | 0.779959 | 0.435415 |
| HNF1A | HNF1A | 78 | −1.74654 | 0.080718 |
| HNF1B | HNF1B | 48 | 0.274363 | 0.783806 |
| HNF4G | HNF4G | 102 | 0.268923 | 0.787989 |
| HOXA10 | HOXA10 | 29 | −0.47125 | 0.637461 |
| HOXA11 | HOXA11 | 14 | −1.41179 | 0.158011 |
| HOXA5 | HOXA5 | 20 | −2.78743 | 0.005313 |
| HOXA9 | HOXA9 | 38 | 1.060151 | 0.289076 |
| HOXC13 | HOXC13 | 15 | −0.82797 | 0.40769 |
| HOXC8 | HOXC8 | 15 | −1.58404 | 0.113184 |
| HOXD13 | HOXD13 | 23 | 2.051993 | 0.04017 |
| HSF1 | HSF1 | 115 | 0.134176 | 0.893263 |
| HSPA1B | HSPA1B | 18 | −0.63053 | 0.528346 |
| ID1 | ID1 | 142 | −2.86808 | 0.00413 |
| ID2 | ID2 | 71 | −2.23042 | 0.025719 |
| ID3 | ID3 | 63 | −2.84359 | 0.004461 |
| IFI16 | IFI16 | 17 | −0.04101 | 0.967291 |
| IRF1 | IRF1 | 311 | 1.058916 | 0.289638 |
| IRF2 | IRF2 | 34 | −0.08632 | 0.931208 |
| IRF3 | IRF3 | 179 | 1.663856 | 0.096141 |
| IRF4 | IRF4 | 53 | 1.16537 | 0.243869 |
| IRF5 | IRF5 | 27 | −0.08125 | 0.935243 |
| IRF6 | IRF6 | 1203 | 1.284136 | 0.199095 |
| IRF7 | IRF7 | 33 | −0.23835 | 0.811613 |
| IRF8 | IRF8 | 47 | 0.528977 | 0.596822 |
| ISL1 | ISL1 | 13 | −0.43434 | 0.66404 |
| JUN | JUN | 673 | 3.060137 | 0.002212 |
| JUNB | JUNB | 115 | −0.81085 | 0.417451 |
| JUND | JUND | 359 | 3.282218 | 0.00103 |
| KAT2A | KAT2A | 35 | 1.340154 | 0.180195 |
| KLF1 | KLF1 | 20 | −1.61554 | 0.106194 |
| KLF10 | KLF10 | 32 | −1.68154 | 0.092658 |
| KLF15 | KLF15 | 13 | 0.50017 | 0.616956 |
| KLF2 | KLF2 | 39 | −0.88487 | 0.376225 |
| KLF4 | KLF4 | 126 | −1.3626 | 0.173009 |
| KLF5 | KLF5 | 38 | 1.33999 | 0.180249 |
| KLF6 | KLF6 | 35 | −1.87978 | 0.060138 |
| KLF9 | KLF9 | 11 | −2.04365 | 0.040988 |
| LEF1 | LEF1 | 65 | −0.32435 | 0.745672 |
| LHX2 | LHX2 | 26 | 0.21167 | 0.832364 |
| MAF | MAF | 36 | 0.15297 | 0.878422 |
| MAFF | MAFF | 119 | 0.079839 | 0.936365 |
| MAFK | MAFK | 177 | 0.184701 | 0.853464 |
| MAPK1 | MAPK1 | 26 | −1.38973 | 0.16461 |
| MAX | MAX | 413 | 6.973296 | 3.10E−12 |
| MAZ | MAZ | 12 | 0.52102 | 0.602353 |
| MEF2A | MEF2A | 69 | −0.3792 | 0.704537 |
| MEF2C | MEF2C | 52 | 1.242668 | 0.21399 |
| MEF2D | MEF2D | 13 | −0.36941 | 0.71182 |
| MEIS1 | MEIS1 | 24 | −0.62118 | 0.534482 |
| MEIS2 | MEIS2 | 20 | −1.95293 | 0.050828 |
| MITF | MITF | 80 | −0.92177 | 0.356649 |
| MLXIPL | MLXIPL | 9 | 0.399449 | 0.689563 |
| MRPL40 | MRPL40 | 18 | −0.63824 | 0.523315 |
| MSC | MSC | 87 | −0.49271 | 0.622218 |
| MSX1 | MSX1 | 25 | −2.40653 | 0.016105 |
| MSX2 | MSX2 | 55 | −1.27053 | 0.203895 |
| MTF1 | MTF1 | 27 | −0.33412 | 0.738291 |
| MTRNR2L1 | MTRNR2L1 | 16 | −0.61432 | 0.539004 |
| MXD1 | MXD1 | 21 | 0.771096 | 0.44065 |
| MXI1 | MXI1 | 68 | 1.548788 | 0.121433 |
| MYB | MYB | 89 | 2.119714 | 0.03403 |

TABLE 4-continued

Converter vs. non-converter baseline Master Regulator analysis

| | Regulon | Size | NES | p.value |
|---|---|---|---|---|
| MYBL2 | MYBL2 | 49 | 1.329846 | 0.183569 |
| MYC | MYC | 1307 | 6.630539 | 3.34E−11 |
| MYCN | MYCN | 107 | −0.92136 | 0.356862 |
| NANOG | NANOG | 186 | −2.41909 | 0.015559 |
| NBPF1 | NBPF1 | 30 | −1.38118 | 0.167224 |
| NCOA1 | NCOA1 | 15 | −0.91836 | 0.358429 |
| NCOA3 | NCOA3 | 46 | −0.54863 | 0.583259 |
| NFAT5 | NFAT5 | 34 | 0.110771 | 0.911798 |
| NFATC1 | NFATC1 | 51 | −0.00658 | 0.994749 |
| NFATC4 | NFATC4 | 22 | −0.47439 | 0.635224 |
| NFE2 | NFE2 | 133 | 0.230329 | 0.817836 |
| NFIC | NFIC | 24 | −1.22856 | 0.219239 |
| NFIX | NFIX | 18 | −0.30978 | 0.756726 |
| NFKB1 | NFKB1 | 126 | 0.032244 | 0.974278 |
| NFYA | NFYA | 258 | 2.454322 | 0.014115 |
| NFYB | NFYB | 285 | 0.388634 | 0.697547 |
| NKRF | NKRF | 11 | −0.8646 | 0.38726 |
| NKX2-1 | NKX2-1 | 20 | 0.4038 | 0.68636 |
| NR1I2 | NR1I2 | 14 | 1.005625 | 0.314596 |
| NR1I3 | NR1I3 | 51 | −1.25017 | 0.211239 |
| NR2C2 | NR2C2 | 214 | 2.498588 | 0.012469 |
| NR2F1 | NR2F1 | 25 | −0.93504 | 0.34977 |
| NR2F2 | NR2F2 | 42 | −1.22894 | 0.219096 |
| NR3C1 | NR3C1 | 275 | −0.67159 | 0.501843 |
| NR3C2 | NR3C2 | 40 | −0.55382 | 0.579703 |
| NR4A1 | NR4A1 | 541 | −3.11662 | 0.001829 |
| NR4A2 | NR4A2 | 45 | −1.72408 | 0.084694 |
| NR5A2 | NR5A2 | 21 | −1.49924 | 0.133812 |
| NR6A1 | NR6A1 | 9 | −0.69796 | 0.485204 |
| NRF1 | NRF1 | 404 | 4.353719 | 1.34E−05 |
| NUP214 | NUP214 | 23 | −0.51712 | 0.605073 |
| PAWR | PAWR | 22 | −0.1726 | 0.862968 |
| PAX2 | PAX2 | 37 | −0.19594 | 0.844658 |
| PAX5 | PAX5 | 159 | 0.74832 | 0.454267 |
| PAX6 | PAX6 | 81 | 2.569159 | 0.010195 |
| PAX8 | PAX8 | 42 | −1.19595 | 0.231717 |
| PBX1 | PBX1 | 43 | −1.56217 | 0.118249 |
| PBX3 | PBX3 | 257 | −0.15059 | 0.880296 |
| PDE4DIP | PDE4DIP | 30 | −0.84827 | 0.396287 |
| PDX1 | PDX1 | 35 | −3.06466 | 0.002179 |
| PGR | PGR | 74 | −1.70675 | 0.087868 |
| PI4KA | PI4KA | 21 | −0.49943 | 0.617479 |
| PITX1 | PITX1 | 15 | −1.05999 | 0.289151 |
| PITX2 | PITX2 | 82 | −1.12354 | 0.261207 |
| PLEK | PLEK | 15 | −0.70927 | 0.47816 |
| PMF1 | PMF1 | 24 | −1.44535 | 0.148359 |
| POLR3A | POLR3A | 19 | 0.922368 | 0.356337 |
| POU1F1 | POU1F1 | 20 | 0.123814 | 0.901463 |
| POU2F1 | POU2F1 | 45 | 2.369076 | 0.017833 |
| POU2F2 | POU2F2 | 119 | 1.59509 | 0.110692 |
| POU3F2 | POU3F2 | 168 | −3.55876 | 0.000373 |
| POU5F1 | POU5F1 | 129 | −1.57145 | 0.116079 |
| POU6F1 | POU6F1 | 11 | 0.059949 | 0.952197 |
| PPARA | PPARA | 277 | −1.05335 | 0.29218 |
| PPARD | PPARD | 111 | −0.94907 | 0.342584 |
| PPARG | PPARG | 304 | −1.84617 | 0.064867 |
| PPARGC1A | PPARGC1A | 29 | −0.56708 | 0.570663 |
| PPIL2 | PPIL2 | 20 | −0.71742 | 0.473113 |
| PRAME | PRAME | 22 | 0.271773 | 0.785796 |
| PRDM1 | PRDM1 | 43 | −1.98139 | 0.047547 |
| PROX1 | PROX1 | 29 | 0.171039 | 0.864193 |
| RAB36 | RAB36 | 17 | −0.57724 | 0.563775 |
| RAD21 | RAD21 | 473 | 0.404801 | 0.685624 |
| RARA | RARA | 61 | −1.44521 | 0.1484 |
| RARB | RARB | 44 | −3.47311 | 0.000514 |
| RARG | RARG | 27 | −0.24677 | 0.805085 |
| RBPJ | RBPJ | 70 | −0.82953 | 0.406805 |
| REL | REL | 87 | 0.886843 | 0.375164 |
| RELA | RELA | 106 | −1.10166 | 0.270611 |
| RELB | RELB | 51 | −0.68492 | 0.493391 |
| REST | REST | 172 | −0.67626 | 0.498874 |
| RFX1 | RFX1 | 14 | −0.57575 | 0.564781 |
| RFX5 | RFX5 | 84 | 1.307749 | 0.190959 |
| RORA | RORA | 19 | 0.781685 | 0.434399 |
| RUNX1 | RUNX1 | 245 | −0.22748 | 0.82005 |
| RUNX2 | RUNX2 | 151 | −1.82508 | 0.067989 |

TABLE 4-continued

Converter vs. non-converter baseline Master Regulator analysis

| | Regulon | Size | NES | p.value |
|---|---|---|---|---|
| RUNX3 | RUNX3 | 65 | 0.131457 | 0.895413 |
| RXRA | RXRA | 72 | 1.280295 | 0.200442 |
| SALL1 | SALL1 | 14 | −1.18 | 0.238001 |
| SATB1 | SATB1 | 10 | 0.462061 | 0.644038 |
| SDF2L1 | SDF2L1 | 23 | −0.87616 | 0.380941 |
| SETBP1 | SETBP1 | 59 | −0.14267 | 0.886549 |
| SETDB1 | SETDB1 | 125 | −0.46296 | 0.643395 |
| SIM2 | SIM2 | 36 | 0.467962 | 0.639811 |
| SIN3A | SIN3A | 55 | 2.605818 | 0.009166 |
| SIRT6 | SIRT6 | 39 | 1.743563 | 0.081235 |
| SIX1 | SIX1 | 18 | 1.231365 | 0.218186 |
| SIX5 | SIX5 | 263 | −0.06625 | 0.947176 |
| SKI | SKI | 24 | −0.59419 | 0.552385 |
| SMAD1 | SMAD1 | 75 | −1.54514 | 0.122314 |
| SMAD2 | SMAD2 | 431 | −3.11924 | 0.001813 |
| SMAD3 | SMAD3 | 510 | −3.35926 | 0.000782 |
| SMAD4 | SMAD4 | 167 | −2.0752 | 0.037968 |
| SMAD5 | SMAD5 | 56 | −1.43085 | 0.152472 |
| SMARCA4 | SMARCA4 | 125 | 4.156509 | 3.23E−05 |
| SMARCB1 | SMARCB1 | 117 | 2.335056 | 0.01954 |
| SMC3 | SMC3 | 75 | 1.168808 | 0.242481 |
| SNAI2 | SNAI2 | 64 | −2.32188 | 0.02024 |
| SOX13 | SOX13 | 12 | −0.26968 | 0.787409 |
| SOX17 | SOX17 | 36 | −1.07345 | 0.283068 |
| SOX2 | SOX2 | 184 | −1.84782 | 0.064629 |
| SOX4 | SOX4 | 26 | −0.22655 | 0.820776 |
| SOX9 | SOX9 | 174 | −1.80944 | 0.070383 |
| SP1 | SP1 | 865 | −2.47968 | 0.01315 |
| SP100 | SP100 | 24 | −0.61601 | 0.537885 |
| SP2 | SP2 | 188 | 1.211764 | 0.225603 |
| SP3 | SP3 | 150 | 1.6031 | 0.108913 |
| SP4 | SP4 | 29 | −1.69027 | 0.090977 |
| SPI1 | SPI1 | 284 | −0.15241 | 0.878865 |
| SREBF1 | SREBF1 | 170 | 1.139298 | 0.254579 |
| SREBF2 | SREBF2 | 78 | 0.503728 | 0.614453 |
| SRF | SRF | 293 | 1.940434 | 0.052327 |
| STAT1 | STAT1 | 383 | 0.842839 | 0.399319 |
| STAT2 | STAT2 | 88 | 0.283629 | 0.776695 |
| STAT3 | STAT3 | 598 | 1.421507 | 0.155169 |
| STAT4 | STAT4 | 21 | 1.011493 | 0.311781 |
| STAT5A | STAT5A | 168 | 1.104389 | 0.269425 |
| STAT5B | STAT5B | 25 | −1.52632 | 0.12693 |
| STAT6 | STAT6 | 77 | −0.23499 | 0.814219 |
| SUZ12 | SUZ12 | 151 | −0.80984 | 0.418032 |
| TAF1 | TAF1 | 439 | 5.82917 | 5.57E−09 |
| TAF7 | TAF7 | 70 | −1.03045 | 0.302799 |
| TAL1 | TAL1 | 162 | −1.26458 | 0.206021 |
| TBP | TBP | 184 | 4.1589 | 3.20E−05 |
| TBX2 | TBX2 | 39 | 0.630216 | 0.528553 |
| TBX3 | TBX3 | 25 | 0.495094 | 0.620534 |
| TBX5 | TBX5 | 18 | −2.56321 | 0.010371 |
| TCF12 | TCF12 | 165 | −0.39208 | 0.694998 |
| TCF3 | TCF3 | 12 | −1.11343 | 0.265524 |
| TCF4 | TCF4 | 391 | 0.753801 | 0.450969 |
| TCF7L1 | TCF7L1 | 15 | 0.30834 | 0.757823 |
| TCF7L2 | TCF7L2 | 49 | −0.91532 | 0.360021 |
| TEF | TEF | 23 | −0.62575 | 0.531482 |
| TFAM | TFAM | 16 | −0.27248 | 0.785252 |
| TFAP2A | TFAP2A | 385 | 1.33025 | 0.183436 |
| TFAP2C | TFAP2C | 153 | 2.376242 | 0.01749 |
| TFE3 | TFE3 | 18 | −0.41694 | 0.67672 |
| TGIF1 | TGIF1 | 19 | 0.511829 | 0.608771 |
| THAP1 | THAP1 | 44 | 0.007277 | 0.994194 |
| THRB | THRB | 14 | −0.46604 | 0.641183 |
| TP53 | TP53 | 1576 | −6.57724 | 4.79E−11 |
| TRIM28 | TRIM28 | 45 | 0.695178 | 0.486944 |
| TSC22D3 | TSC22D3 | 61 | −1.27922 | 0.200819 |
| TWIST1 | TWIST1 | 80 | 1.198189 | 0.230844 |
| USF1 | USF1 | 30 | 0.616252 | 0.537728 |
| USF2 | USF2 | 236 | 1.231038 | 0.218309 |
| VDR | VDR | 113 | −0.72764 | 0.466833 |
| XBP1 | XBP1 | 66 | 0.414696 | 0.678365 |
| XRCC4 | XRCC4 | 28 | −0.79178 | 0.428489 |
| YBX1 | YBX1 | 42 | −0.63687 | 0.524206 |
| YY1 | YY1 | 410 | 3.781417 | 0.000156 |
| ZBTB17 | ZBTB17 | 20 | −0.38443 | 0.700662 |

TABLE 4-continued

Converter vs. non-converter baseline Master Regulator analysis

| | Regulon | Size | NES | p.value |
|---|---|---|---|---|
| ZBTB33 | ZBTB33 | 151 | −1.95137 | 0.051013 |
| ZBTB7A | ZBTB7A | 163 | 0.938493 | 0.347991 |
| ZEB1 | ZEB1 | 118 | −0.74247 | 0.457803 |
| ZEB2 | ZEB2 | 20 | −0.89984 | 0.368205 |
| ZNF143 | ZNF143 | 30 | −0.98471 | 0.324765 |
| ZNF263 | ZNF263 | 245 | −0.16919 | 0.865649 |
| ZNF274 | ZNF274 | 65 | 0.593574 | 0.552797 |
| ZZZ3 | ZZZ3 | 21 | 0.038971 | 0.968913 |

TABLE 5

| 14 Gene Lineage Plasticity Risk Signature |
|---|
| RNF43 |
| SNRPF |
| TRABD2A |
| NDUFA12 |
| GAS2L3 |
| RPS24 |
| DNA2 |
| RP5-857K21.10 |
| POC1B |
| ADK |
| ATP5B |
| XPOT |
| SLCO1B3 |
| RHOBTB1 |

TABLE 6

Genes downregulated in progression versus baseline in converters

| Gene | log2 fold change | p adjusted |
|---|---|---|
| GJB1 | −13.0109 | 0.00803528 |
| KRT19 | −12.4296 | 0.009995189 |
| MSMB | −10.9755 | 1.60052E−12 |
| KLK4 | −10.8022 | 6.07743E−28 |
| RFX6 | −10.7898 | 2.69827E−09 |
| SPDEF | −10.5975 | 1.95528E−06 |
| PRAC1 | −10.586 | 2.19387E−16 |
| TRPM8 | −10.432 | 6.84759E−10 |
| CWH43 | −10.4251 | 1.21947E−12 |
| SFTPA2 | −10.4246 | 6.36253E−14 |
| KLK2 | −10.12 | 4.5295E−14 |
| RP11-64K7.1 | −9.84876 | 6.00493E−08 |
| C1orf116 | −9.5854 | 3.74956E−32 |
| TRPV6 | −9.46577 | 1.60052E−12 |
| PCAT14 | −9.45153 | 1.05491E−08 |
| KLK3 | −9.31504 | 5.91494E−38 |
| LMAN1L | −9.2235 | 3.82153E−05 |
| FAM155B | −9.12385 | 3.15397E−05 |
| SFT2D3 | −9.05073 | 0.014343495 |
| CLDN8 | −9.0205 | 0.000247776 |
| PLPPR1 | −9.01465 | 7.62753E−06 |
| AR | −9.00786 | 2.67485E−20 |
| CH17-335B8.6 | −8.98895 | 5.5873E−05 |
| GCG | −8.9036 | 0.002364738 |
| RP11-250B16.1 | −8.8774 | 6.18409E−08 |
| LUZP2 | −8.84452 | 8.01584E−08 |
| ELF5 | −8.828 | 1.54204E−05 |
| HOXB13 | −8.64854 | 1.40708E−17 |
| NKX3-1 | −8.6224 | 3.94512E−21 |
| RP11-167H9.6 | −8.57309 | 0.001755056 |
| AP1M2 | −8.56433 | 0.000299706 |
| RP11-386M24.6 | −8.49415 | 6.31748E−09 |
| COLCA1 | −8.4758 | 2.22009E−11 |
| NUDT11 | −8.42477 | 0.000117825 |
| MAL2 | −8.36678 | 4.5655E−06 |
| MAGEA1 | −8.3178 | 0.025761966 |

TABLE 6-continued

Genes downregulated in progression versus baseline in converters

| Gene | log2 fold change | p adjusted |
|---|---|---|
| ALDH3B2 | −8.29458 | 0.000408765 |
| ELFN2 | −8.25871 | 2.0192E−07 |
| BMPR1B | −8.22216 | 1.13195E−09 |
| SLC9A2 | −8.22212 | 3.93176E−05 |
| GDF15 | −8.20863 | 3.24736E−08 |
| RIPK4 | −8.16098 | 0.000679994 |
| RP6-201G10.2 | −8.13008 | 0.009363237 |
| MB | −8.08018 | 5.57196E−05 |
| RP11-810K23.10 | −8.06303 | 0.013754538 |
| RP11-414J4.2 | −8.04941 | 1.95528E−06 |
| PRR36 | −8.04044 | 0.002062771 |
| GLYATL1 | −8.03801 | 8.01584E−08 |
| OR51E2 | −8.03443 | 5.29546E−08 |
| VSTM2L | −8.01538 | 0.001159402 |
| RP11-191G24.2 | −7.98022 | 0.000394074 |
| CPNE4 | −7.97461 | 1.81751E−05 |
| ZG16B | −7.91661 | 8.89766E−06 |
| STEAP2 | −7.90516 | 6.27827E−19 |
| TGM3 | −7.90155 | 0.000201653 |
| KB-1562D12.1 | −7.85336 | 0.006725243 |
| MUM1L1 | −7.81099 | 0.047267105 |
| FOXA1 | −7.78551 | 3.8039E−07 |
| SSTR1 | −7.75964 | 2.15594E−05 |
| FOLH1 | −7.73365 | 2.8238E−05 |
| NPY2R | −7.70357 | 0.001820183 |
| GPR81 | −7.67445 | 0.003315652 |
| PLA2G4F | −7.6702 | 2.86056E−05 |
| AP001615.9 | −7.64992 | 0.00281238 |
| RP11-664D7.4 | −7.63551 | 2.30599E−06 |
| TMPRSS2 | −7.61592 | 1.57797E−12 |
| CBLC | −7.5637 | 0.011752953 |
| LONRF2 | −7.55205 | 7.8229E−08 |
| PRAC2 | −7.50435 | 0.006941479 |
| KLKP1 | −7.40505 | 2.49362E−05 |
| CTD-2008P7.9 | −7.40308 | 0.031968996 |
| ZDHHC8P | −7.39731 | 0.000105089 |
| PTPRT | −7.39084 | 1.53606E−08 |
| KLK15 | −7.38721 | 0.00151056 |
| HOXA11-AS1 | −7.38246 | 0.000318881 |
| MSI1 | −7.38125 | 0.009341293 |
| RGS11 | −7.35431 | 1.15968E−05 |
| ITIH6 | −7.30192 | 0.013754538 |
| CNNM1 | −7.295 | 1.0376E−12 |
| RP11-96O20.1 | −7.28528 | 2.69827E−09 |
| ESRP1 | −7.27842 | 3.9422E−06 |
| RP11-44F14.8 | −7.2738 | 0.000169539 |
| OPRK1 | −7.26447 | 0.011482303 |
| OVOL1 | −7.22031 | 0.019243098 |
| RP11-23F23.2 | −7.206 | 0.000510792 |
| CTC-429C10.4 | −7.19953 | 0.002543297 |
| TSPAN1 | −7.16544 | 1.77922E−12 |
| B4GALNT4 | −7.15865 | 0.015346028 |
| HNF1B | −7.14867 | 0.006147776 |
| DPY19L2P4 | −7.14349 | 0.018382137 |
| RP11-217E22.2 | −7.09768 | 0.007346357 |
| BRINP3 | −7.09246 | 0.007726148 |
| KCNQ4 | −7.08721 | 0.01062877 |
| LPAR3 | −7.0795 | 2.32188E−09 |
| RP11-429J17.8 | −7.03507 | 9.4023E−06 |
| ACPP | −7.03063 | 2.29033E−08 |
| NKAIN1 | −7.01909 | 0.000140179 |
| SLC6A11 | −6.99287 | 1.19755E−05 |
| CKMT1B | −6.97352 | 2.85313E−05 |
| AC005077.14 | −6.92458 | 0.012413722 |
| EPCAM | −6.91034 | 1.49312E−05 |
| CHMP4C | −6.90771 | 0.000103013 |
| CLDN3 | −6.88946 | 5.80941E−05 |
| C8orf34 | −6.87524 | 0.003315652 |
| EHF | −6.86723 | 2.49362E−05 |
| CLDN4 | −6.8506 | 0.000421405 |
| TMSB15A | −6.83338 | 0.022191671 |
| SIM2 | −6.81808 | 3.0951E−05 |
| CDH7 | −6.80255 | 0.001317177 |
| CREB3L1 | −6.78654 | 5.38642E−19 |
| RET | −6.76795 | 0.006752055 |

TABLE 6-continued

Genes downregulated in progression versus baseline in converters

| Gene | log2 fold change | p adjusted |
|---|---|---|
| HS6ST3 | −6.74427 | 0.000248805 |
| SHANK2 | −6.74014 | 2.30599E−06 |
| TMEFF2 | −6.73602 | 0.000219103 |
| HSD17B6 | −6.72389 | 3.63729E−05 |
| RP11-810K23.9 | −6.69377 | 0.048963223 |
| RP11-386M24.3 | −6.67882 | 0.011406542 |
| IL20RA | −6.6682 | 0.000394074 |
| CHRNA2 | −6.66762 | 0.02380943 |
| CRABP2 | −6.64933 | 0.000520944 |
| ZBED9 | −6.59905 | 0.00365828 |
| TSPAN8 | −6.59719 | 0.01310687 |
| DNASE2B | −6.5658 | 0.020111479 |
| ARFGEF3 | −6.5653 | 1.43252E−16 |
| CTD-2315M5.2 | −6.5475 | 0.001864013 |
| CRISP3 | −6.52223 | 0.007176935 |
| PDZK1IP1 | −6.51569 | 0.01055954 |
| STEAP1 | −6.49332 | 1.45863E−09 |
| PBOV1 | −6.48531 | 0.000131516 |
| SPTBN2 | −6.4581 | 0.000851134 |
| RAB3B | −6.37894 | 1.62558E−08 |
| SYT7 | −6.37818 | 2.77749E−05 |
| RP11-572M18.1 | −6.3717 | 0.029303804 |
| SEMA3C | −6.36548 | 6.49127E−19 |
| COL2A1 | −6.35909 | 5.8515E−05 |
| FRMPD4 | −6.35095 | 0.046924645 |
| RP4-568C11.4 | −6.33688 | 0.000190283 |
| OVOL2 | −6.3276 | 0.042698538 |
| CUX2 | −6.25239 | 0.000319499 |
| TFAP2C | −6.24995 | 0.007446394 |
| RIPPLY3 | −6.23858 | 0.025465136 |
| DNAJC22 | −6.15536 | 0.038581579 |
| HIST3H2A | −6.14943 | 2.47998E−05 |
| FAM3B | −6.12534 | 0.000166735 |
| CHRM1 | −6.10673 | 0.024066227 |
| C1orf210 | −6.10671 | 0.009161256 |
| TRGC1 | −6.10126 | 0.000368444 |
| GRHL2 | −6.07235 | 4.31758E−06 |
| EPN3 | −6.05967 | 0.004856004 |
| CTD-2626G11.2 | −6.03012 | 0.015236703 |
| MAPK8IP2 | −6.01836 | 0.002676092 |
| CAMSAP3 | −6.0032 | 0.018436013 |
| GLB1L2 | −5.98958 | 0.002169017 |
| ARL4P | −5.98621 | 0.019243098 |
| PKNOX2 | −5.9705 | 0.001537648 |
| PROM2 | −5.95201 | 0.000150439 |
| RP11-794G24.1 | −5.93328 | 0.006307743 |
| ARHGAP6 | −5.90103 | 3.23698E−06 |
| C3orf80 | −5.88771 | 0.011706175 |
| CERS1 | −5.85838 | 0.007844838 |
| KAZALD1 | −5.85645 | 0.000413558 |
| KCNG1 | −5.84824 | 0.031523396 |
| AGTR1 | −5.83595 | 9.15929E−07 |
| GAL | −5.83458 | 0.004055001 |
| PPP1R1B | −5.82851 | 3.13653E−09 |
| RANBP3L | −5.81794 | 2.51666E−06 |
| PRSS8 | −5.81696 | 0.005362879 |
| PLPP1 | −5.75925 | 2.67485E−20 |
| GLYATL1P1 | −5.75464 | 0.013457395 |
| SAMD5 | −5.74866 | 2.42795E−08 |
| EPHA7 | −5.72406 | 0.026780088 |
| TACSTD2 | −5.6688 | 1.03652E−05 |
| PRR15L | −5.65178 | 0.001562489 |
| F12 | −5.63147 | 0.001590333 |
| PYCR1 | −5.59224 | 0.002212432 |
| KRT8 | −5.58961 | 0.001317177 |
| KDF1 | −5.58481 | 0.025166394 |
| KLF15 | −5.57358 | 0.000510792 |
| RP1-239B22.5 | −5.57151 | 0.030116743 |
| XDH | −5.54559 | 0.000930733 |
| ANKRD30A | −5.54261 | 0.001549402 |
| KCNC2 | −5.53619 | 0.035899302 |
| SLC44A4 | −5.53579 | 0.000389098 |
| TMC4 | −5.51246 | 0.001097835 |
| CLDN1 | −5.50523 | 0.00230044 |
| NWD1 | −5.47963 | 1.12618E−05 |

TABLE 6-continued

Genes downregulated in progression versus baseline in converters

| Gene | log2 fold change | p adjusted |
|---|---|---|
| LAMA1 | −5.47147 | 0.012383175 |
| RP11-44F14.2 | −5.47147 | 0.000254976 |
| ERBB3 | −5.45723 | 8.17457E−06 |
| CAPN13 | −5.44675 | 0.007996556 |
| SH2D4A | −5.44673 | 0.00031238 |
| GATA2 | −5.43639 | 6.05752E−08 |
| CRYM | −5.4186 | 0.003834794 |
| HPN | −5.39975 | 0.000610051 |
| ARHGEF38 | −5.3921 | 1.4071E−05 |
| KLK11 | −5.38859 | 0.042443384 |
| TMEM125 | −5.38713 | 0.008470304 |
| RP11-61N20.3 | −5.37734 | 0.020600986 |
| RP11-887P2.1 | −5.36726 | 0.00271796 |
| ST6GALNAC1 | −5.34964 | 0.002310415 |
| BCYRN1 | −5.34173 | 0.000394074 |
| RORB | −5.33749 | 0.001313938 |
| RP11-680C21.1 | −5.33702 | 0.027161703 |
| MUC13 | −5.33548 | 0.008421801 |
| UNC5A | −5.33402 | 0.014974489 |
| WNT7B | −5.33287 | 0.028295215 |
| MAOA | −5.3151 | 2.32964E−05 |
| BRSK2 | −5.31409 | 0.041483081 |
| ONECUT2 | −5.31276 | 0.002495169 |
| PRR16 | −5.29134 | 3.63871E−09 |
| LAD1 | −5.28453 | 0.00175777 |
| TTC6 | −5.28105 | 0.000764496 |
| TRGV9 | −5.274 | 0.001319505 |
| ERVMER34-1 | −5.2629 | 0.006941479 |
| PDE9A | −5.25653 | 0.000256129 |
| NFIX | −5.24719 | 9.0469E−16 |
| SLC45A3 | −5.23953 | 6.09221E−05 |
| KRT18 | −5.23594 | 0.000916193 |
| CGREF1 | −5.2326 | 0.000520944 |
| FAXC | −5.22737 | 0.004551851 |
| RIMS1 | −5.21989 | 0.023229561 |
| CKMT1A | −5.21458 | 0.000510792 |
| KIF5C | −5.21069 | 6.98142E−06 |
| TUFT1 | −5.19053 | 0.010580032 |
| CGN | −5.18038 | 0.005195388 |
| DCDC2 | −5.16915 | 0.00601495 |
| LYPD6B | −5.14802 | 0.03778331 |
| SCNN1A | −5.13995 | 0.015531057 |
| FRAS1 | −5.13625 | 0.018371812 |
| KCND3 | −5.11214 | 2.50126E−06 |
| AQP3 | −5.08797 | 0.00041265 |
| TBX3 | −5.07588 | 0.000807785 |
| PCDHB2 | −5.06229 | 0.005053276 |
| PLA2G2A | −5.0594 | 0.004403906 |
| SLC30A4 | −5.05773 | 2.11383E−07 |
| DNAJC12 | −5.05297 | 0.008854581 |
| GSTO2 | −5.03542 | 0.019916132 |
| PCDHB16 | −5.03101 | 0.001506409 |
| MYH14 | −5.00681 | 0.038148283 |
| FAM47E-STBD1 | −5.00384 | 0.001530784 |
| OR7E47P | −4.99846 | 0.027205581 |
| CGNL1 | −4.99223 | 1.08457E−06 |
| SV2C | −4.98913 | 0.00492018 |
| RAMP1 | −4.96574 | 0.019674785 |
| ESRP2 | −4.96328 | 0.000637971 |
| ASIC1 | −4.91851 | 8.98808E−05 |
| LRRC26 | −4.91831 | 0.025465136 |
| RP11-159H10.3 | −4.89845 | 0.022784159 |
| 01-Mar | −4.87761 | 1.33169E−05 |
| C1orf168 | −4.87428 | 0.010816456 |
| ADGRV1 | −4.86761 | 0.000834175 |
| RP11-123K3.4 | −4.84725 | 0.017085905 |
| C9orf152 | −4.84208 | 1.34448E−06 |
| RAB6C | −4.83158 | 0.030174703 |
| RAB27B | −4.81706 | 3.19313E−07 |
| COBL | −4.81559 | 0.000878147 |
| TMC5 | −4.80912 | 4.21366E−11 |
| CLGN | −4.79296 | 0.001549402 |
| RAP1GAP | −4.78347 | 1.60818E−06 |
| USP43 | −4.77611 | 0.043299512 |
| GYG2 | −4.76148 | 0.031360574 |

TABLE 6-continued

Genes downregulated in progression versus baseline in converters

| Gene | log2 fold change | p adjusted |
|---|---|---|
| MAP7 | −4.68236 | 2.70581E−05 |
| MESP1 | −4.68154 | 0.000341157 |
| SLC16A14 | −4.63291 | 1.84154E−06 |
| TMEM98 | −4.6317 | 0.001086483 |
| EPDR1 | −4.62479 | 0.000150439 |
| NIPAL1 | −4.62291 | 0.003347226 |
| NBEAP1 | −4.61603 | 0.036190951 |
| NAP1L2 | −4.60869 | 0.01967406 |
| ENDOD1 | −4.59012 | 2.22009E−11 |
| RP11-480I12.5 | −4.58859 | 0.038581579 |
| TMEM184A | −4.5783 | 0.008551888 |
| EDA | −4.57727 | 0.003168575 |
| C6orf132 | −4.56958 | 0.034209994 |
| MLPH | −4.56818 | 0.001159402 |
| TMEM30B | −4.55692 | 0.001313938 |
| CHRNA5 | −4.54936 | 0.001615076 |
| SOX9 | −4.52975 | 0.015273621 |
| PODN | −4.52946 | 0.008454248 |
| RHPN2 | −4.52081 | 0.000520944 |
| RP11-426A6.7 | −4.51391 | 0.004205484 |
| FAM160A1 | −4.45517 | 0.000145626 |
| SHROOM1 | −4.42189 | 1.48075E−06 |
| PAX9 | −4.39074 | 0.012964059 |
| SLC1A2 | −4.35607 | 0.030222612 |
| ZP3 | −4.35295 | 0.044794635 |
| IRF6 | −4.35264 | 7.07542E−06 |
| PCDHB5 | −4.33769 | 0.031523396 |
| MARVELD3 | −4.33581 | 0.008421801 |
| RP11-747H7.3 | −4.3352 | 0.017354855 |
| LRRIQ1 | −4.32898 | 0.047913842 |
| SHISA6 | −4.32686 | 0.000854246 |
| DNAH5 | −4.3124 | 2.06066E−05 |
| FAM83H | −4.31012 | 0.027604189 |
| APOD | −4.3051 | 0.032178145 |
| CAB39L | −4.27946 | 4.41046E−05 |
| GABRB3 | −4.27892 | 0.000807785 |
| ABCC6 | −4.19027 | 0.016010283 |
| ELOVL2 | −4.18657 | 0.024445786 |
| CLDN7 | −4.16232 | 0.007706621 |
| SPOCK1 | −4.15854 | 0.007726148 |
| EEF1A2 | −4.15155 | 0.006294815 |
| SYBU | −4.14684 | 1.47472E−06 |
| RP11-44F14.9 | −4.1427 | 0.035513706 |
| ZBTB16 | −4.1426 | 0.011262349 |
| MANSC1 | −4.1268 | 0.003655544 |
| RP11-34613.4 | −4.11864 | 0.014181168 |
| CRISPLD1 | −4.08335 | 0.000135526 |
| ENPP3 | −4.08046 | 0.009363237 |
| SIX4 | −4.07614 | 0.009605191 |
| GREB1 | −4.07006 | 0.000239832 |
| REEP6 | −4.06947 | 0.024043573 |
| RPLP0P2 | −4.06105 | 0.0047813 |
| SIX1 | −4.01941 | 0.04803082 |
| OR51E1 | −4.01531 | 0.009188572 |
| F2RL1 | −4.00093 | 0.003669078 |
| DLX1 | −3.99995 | 0.001131965 |
| DPP4 | −3.99894 | 0.019919664 |
| DRAIC | −3.99642 | 3.34027E−05 |
| SERINC2 | −3.98847 | 0.027735755 |
| PLEKHS1 | −3.98619 | 0.006147776 |
| PODXL2 | −3.98613 | 0.049456799 |
| OSR2 | −3.97873 | 0.041789964 |
| PRKD1 | −3.97692 | 0.014936402 |
| F5 | −3.97154 | 0.000168314 |
| RP11-255B23.3 | −3.96763 | 0.006004447 |
| HID1 | −3.95023 | 0.023095214 |
| ATP7B | −3.93918 | 0.014537241 |
| CMTM4 | −3.92948 | 0.001615076 |
| MAPT | −3.90127 | 0.010183334 |
| TACC2 | −3.89662 | 0.008421801 |
| BCAM | −3.87701 | 0.02627901 |
| CTD-2331H7.1 | −3.8732 | 0.010412188 |
| TSPAN6 | −3.86879 | 0.026094201 |
| SLC2A12 | −3.8634 | 0.008136488 |
| RP11-680F20.10 | −3.85507 | 0.030116743 |

TABLE 6-continued

Genes downregulated in progression versus baseline in converters

| Gene | log2 fold change | p adjusted |
|---|---|---|
| WWC1 | −3.85469 | 0.006147776 |
| BEND4 | −3.85284 | 0.00167161 |
| HPGD | −3.8522 | 0.040413829 |
| SGMS2 | −3.83276 | 0.001360859 |
| CD9 | −3.83214 | 0.002988409 |
| GUCY1A3 | −3.83071 | 3.91721E−06 |
| SORBS2 | −3.80372 | 0.00033472 |
| RP4-617A9.4 | −3.79698 | 2.13211E−05 |
| RAB25 | −3.7958 | 0.016533393 |
| TC2N | −3.77787 | 0.013369341 |
| KIAA1324 | −3.77572 | 0.005589822 |
| ARHGEF26 | −3.77026 | 0.001077207 |
| NUPR1 | −3.74028 | 0.003847893 |
| MPV17L | −3.72587 | 0.002868759 |
| RP11-752L20.3 | −3.71907 | 0.005312611 |
| STYK1 | −3.71333 | 0.028582815 |
| RP11-173P15.3 | −3.71217 | 0.001627965 |
| PCDH1 | −3.67758 | 0.002427901 |
| CTD-2008A1.2 | −3.67627 | 3.99898E−05 |
| SMPDL3B | −3.66277 | 0.000192708 |
| AMACR | −3.6508 | 3.68572E−05 |
| NPDC1 | −3.63564 | 2.06066E−05 |
| TTC39A | −3.61882 | 0.012515436 |
| TMEM54 | −3.61552 | 0.021942343 |
| SLC38A11 | −3.61052 | 0.034502376 |
| DAB1 | −3.6031 | 0.048696304 |
| PMEPA1 | −3.58662 | 0.002800716 |
| FAM110B | −3.58115 | 0.019109222 |
| RAB3D | −3.56739 | 0.001319505 |
| KIAA1549 | −3.56152 | 0.012964059 |
| P3H2 | −3.55822 | 0.017873352 |
| RP11-588K22.2 | −3.55621 | 0.017269032 |
| ALDH1A3 | −3.55009 | 0.00065603 |
| TOM1L1 | −3.52686 | 0.005571832 |
| RP11-650L12.2 | −3.52568 | 0.039535023 |
| ILDR1 | −3.52149 | 0.035659151 |
| STEAP4 | −3.51282 | 0.000119443 |
| ZNF704 | −3.51103 | 0.007065518 |
| PLCB4 | −3.50997 | 0.029596135 |
| CREB3L4 | −3.50844 | 0.001319505 |
| TSPAN9 | −3.47647 | 0.042701585 |
| ANK3 | −3.47157 | 7.78081E−05 |
| RPS6KA6 | −3.43505 | 0.029656097 |
| PRNCR1 | −3.42974 | 0.032653896 |
| PDZRN3 | −3.4276 | 0.008421801 |
| AC027612.6 | −3.42116 | 0.038581579 |
| FASN | −3.41871 | 0.025208732 |
| GRIP1 | −3.41355 | 0.001456508 |
| PPM1H | −3.39951 | 0.00163171 |
| RGS2 | −3.39419 | 0.040691341 |
| TMEM136 | −3.38738 | 7.17713E−05 |
| MIPOL1 | −3.3837 | 0.010807021 |
| REPS2 | −3.37405 | 0.000145626 |
| ARHGEF37 | −3.37274 | 0.006941479 |
| RP11-48B3.4 | −3.36568 | 0.019721003 |
| CDH1 | −3.35542 | 0.012768592 |
| MPZL2 | −3.35329 | 0.028809917 |
| RP5-857K21.9 | −3.33954 | 0.007859266 |
| COLEC12 | −3.33188 | 0.005759039 |
| BAIAP2 | −3.32769 | 0.031523396 |
| NECTIN3 | −3.32615 | 0.003315309 |
| SORD | −3.31931 | 0.00156896 |
| GNAI1 | −3.30086 | 0.022933693 |
| ALOX15 | −3.30058 | 0.027196875 |
| AP000689.8 | −3.29912 | 0.016177969 |
| SLC12A8 | −3.26725 | 0.013595212 |
| COL1A2 | −3.25913 | 0.000181462 |
| ACACA | −3.24295 | 0.006345868 |
| KAZN | −3.23967 | 0.038516516 |
| USP54 | −3.22198 | 0.013128708 |
| SLC10A5 | −3.22123 | 0.011482303 |
| MARVELD2 | −3.21197 | 0.009194773 |
| DDAH1 | −3.20936 | 0.000804259 |
| WNK3 | −3.20931 | 0.019840929 |
| MICAL2 | −3.206 | 0.001633876 |

TABLE 6-continued

Genes downregulated in progression versus baseline in converters

| Gene | log2 fold change | p adjusted |
|---|---|---|
| C1orf226 | −3.20504 | 0.016804516 |
| CXADR | −3.17825 | 0.012198713 |
| TRPM4 | −3.17715 | 0.041062369 |
| VIPR1 | −3.17145 | 0.007241708 |
| SLC39A6 | −3.14717 | 0.000348718 |
| COL1A1 | −3.13837 | 3.63729E−05 |
| TBC1D30 | −3.13418 | 0.012247234 |
| PLPPR4 | −3.125 | 0.028582815 |
| TMEM56 | −3.10976 | 0.011482303 |
| ABCC4 | −3.10395 | 0.000139166 |
| CERS4 | −3.10235 | 0.016170818 |
| ABCA3 | −3.09421 | 0.030503102 |
| LAMA3 | −3.07328 | 0.043727032 |
| SOCS2 | −3.05591 | 0.0279578 |
| SLC16A1 | −3.05516 | 0.024095115 |
| PDGFA | −3.05248 | 5.06499E−05 |
| TUB | −3.02892 | 0.03033514 |
| OLFM2 | −3.02779 | 0.030082505 |
| RDH11 | −3.02169 | 0.002169017 |
| SERINC5 | −3.0213 | 0.0068097 |
| MT-ATP8 | −3.01865 | 0.00653448 |
| LGR4 | −3.00892 | 0.003930701 |
| RASEF | −3.00841 | 0.042466454 |
| CANT1 | −3.00341 | 0.005833148 |
| COL5A2 | −3.00162 | 0.000949378 |
| GREB1L | −3.00015 | 0.000868222 |
| OCLN | −2.99631 | 0.010988211 |
| GPRC5C | −2.99309 | 0.049622084 |
| AK4 | −2.99069 | 0.00428589 |
| OPHN1 | −2.98333 | 0.029393141 |
| SRPX2 | −2.97978 | 0.044733512 |
| EFNA1 | −2.97167 | 0.024903478 |
| REXO2 | −2.97129 | 0.000139166 |
| MYC | −2.96642 | 4.73503E−05 |
| MPC2 | −2.96398 | 6.81855E−05 |
| ELOVL7 | −2.9442 | 0.022922237 |
| LRP11 | −2.92824 | 0.005571832 |
| GLRX2 | −2.89483 | 0.000408745 |
| NAALADL2 | −2.88324 | 0.023804551 |
| NECTIN4 | −2.87763 | 0.027750065 |
| ARHGAP28 | −2.87728 | 0.031483355 |
| MGST1 | −2.87549 | 0.021267136 |
| PRSS23 | −2.86674 | 0.011482303 |
| MT-ND1 | −2.86064 | 0.000105476 |
| MTRNR2L1 | −2.85414 | 0.033069909 |
| SLC9A3R2 | −2.85142 | 0.00286168 |
| TPD52 | −2.84039 | 0.000888655 |
| SLC12A2 | −2.83619 | 0.000252516 |
| FAM210B | −2.81462 | 0.000548103 |
| FAM174B | −2.80768 | 0.028192137 |
| SLC26A4 | −2.80541 | 0.042466454 |
| PLEKHH1 | −2.79816 | 0.044509632 |
| CMBL | −2.79137 | 0.028741604 |
| NEO1 | −2.77968 | 0.001893041 |
| TPD52L1 | −2.77444 | 0.023814858 |
| SYTL2 | −2.75795 | 0.002275789 |
| ABHD11 | −2.75729 | 0.04988753 |
| UGDH | −2.75306 | 0.016533393 |
| PPP3CA | −2.75253 | 0.002294732 |
| RP5-857K21.8 | −2.73877 | 0.006429423 |
| CAMKK2 | −2.73839 | 0.005597112 |
| PCBD1 | −2.73249 | 0.025465136 |
| DCXR | −2.71061 | 0.029157884 |
| STON1 | −2.70229 | 0.017595961 |
| HACD2 | −2.68314 | 0.000641059 |
| MALL | −2.67995 | 0.014548359 |
| TRIB3 | −2.677 | 0.011262349 |
| TXNDC16 | −2.65465 | 0.006307743 |
| ENTPD5 | −2.65234 | 0.000619674 |
| SH3D19 | −2.64312 | 0.017734625 |
| MTRNR2L12 | −2.62665 | 0.031384701 |
| PDLIM5 | −2.62535 | 0.006208061 |
| MAP9 | −2.61985 | 0.001949315 |
| CYB561 | −2.60219 | 0.038266611 |
| SLC7A8 | −2.59571 | 0.01337898 |

TABLE 6-continued

Genes downregulated in progression versus baseline in converters

| Gene | log2 fold change | p adjusted |
|---|---|---|
| ABCB6 | −2.58659 | 0.032581945 |
| CD276 | −2.56663 | 0.029848465 |
| NBL1 | −2.55827 | 0.049857902 |
| STC2 | −2.55729 | 0.030974193 |
| THRB | −2.55343 | 0.009443348 |
| FLNB | −2.53289 | 0.027035537 |
| DEGS1 | −2.53173 | 0.009443348 |
| TRIB1 | −2.51806 | 0.006917927 |
| PDIA5 | −2.51687 | 0.047522688 |
| ITGB5 | −2.49643 | 0.019064569 |
| AIF1L | −2.49 | 0.030748717 |
| PDE3B | −2.48754 | 0.008470304 |
| NME4 | −2.48399 | 0.009310586 |
| SLC19A2 | −2.47665 | 0.03778331 |
| TMEM106C | −2.4741 | 0.012908923 |
| FAM213A | −2.45981 | 0.022167668 |
| PXDN | −2.45974 | 0.006429423 |
| GPR160 | −2.45061 | 0.003988421 |
| MT-ND2 | −2.44487 | 0.012075163 |
| ARHGAP29 | −2.44087 | 0.012060269 |
| MT-ATP6 | −2.43815 | 0.012681365 |
| MAML3 | −2.434 | 0.013224523 |
| RP11-96D1.11 | −2.43379 | 0.027908918 |
| JUN | −2.42316 | 0.029656097 |
| MT-ND4L | −2.42155 | 0.002012454 |
| TRIM68 | −2.41935 | 0.007673209 |
| FSTL1 | −2.40755 | 0.023289438 |
| ENC1 | −2.40286 | 0.042443384 |
| SMOC2 | −2.39778 | 0.027750065 |
| SETD7 | −2.39332 | 0.016010283 |
| ZNF615 | −2.39309 | 0.015444327 |
| RP11-701H24.4 | −2.39055 | 0.028582815 |
| LCLAT1 | −2.38519 | 0.002531903 |
| KCTD15 | −2.37194 | 0.016568111 |
| MT-ND6 | −2.33954 | 0.048113062 |
| TRIQK | −2.33685 | 0.00696301 |
| MGST2 | −2.33313 | 0.015444327 |
| ZBTB10 | −2.33043 | 0.004194537 |
| ACADSB | −2.31812 | 0.01333021 |
| FKBP4 | −2.3173 | 0.046277831 |
| KIF21A | −2.31453 | 0.03778331 |
| MTRNR2L8 | −2.30359 | 0.026633792 |
| NUDT19 | −2.29356 | 0.009058911 |
| AKAP1 | −2.28996 | 0.019721003 |
| ACSL3 | −2.26876 | 0.006941479 |
| MT-ND4 | −2.24326 | 0.0071878 |
| SLC25A37 | −2.23936 | 0.020691978 |
| NTN4 | −2.23137 | 0.04988753 |
| SLC7A11 | −2.22381 | 0.016533393 |
| PRUNE2 | −2.21993 | 0.016533393 |
| TOB1 | −2.2117 | 0.038933819 |
| IGF1R | −2.209 | 0.029073077 |
| GGCT | −2.19672 | 0.022651032 |
| TMED2 | −2.18258 | 0.043013224 |
| ERGIC1 | −2.17755 | 0.016600723 |
| PM20D2 | −2.17005 | 0.017085905 |
| GJA1 | −2.16616 | 0.047619299 |
| GNPNAT1 | −2.16346 | 0.039065825 |
| RPS24 | −2.16167 | 0.010279784 |
| MT-CYB | −2.1492 | 0.017734625 |
| SNHG4 | −2.12883 | 0.032665401 |
| THBS1 | −2.12064 | 0.010901468 |
| NECTIN2 | −2.11069 | 0.014537241 |
| AC092296.1 | −2.08196 | 0.025465136 |
| COBLL1 | −2.07932 | 0.049085362 |
| MIA3 | −2.07829 | 0.013778438 |
| TTC7B | −2.06515 | 0.042152661 |
| PUS7 | −2.0614 | 0.037984901 |
| AIDA | −2.05807 | 0.030503102 |
| RP5-857K21.10 | −2.05495 | 0.014508082 |
| SGMS1 | −2.04054 | 0.031891577 |
| CKAP4 | −2.03696 | 0.034778833 |
| ATP2C1 | −2.02364 | 0.027594022 |
| P4HA1 | −2.02335 | 0.038516516 |
| MT-ND5 | −2.01271 | 0.028362793 |

TABLE 6-continued

Genes downregulated in progression versus baseline in converters

| Gene | log2 fold change | p adjusted |
|---|---|---|
| IARS2 | −2.01144 | 0.032521008 |
| LRIG1 | −2.0102 | 0.047027728 |
| SPARC | −2.00324 | 0.024869268 |
| ATP5B | −1.99582 | 0.030082505 |
| MT-RNR2 | −1.98933 | 0.023760359 |
| FH | −1.96081 | 0.029353507 |
| CDK2AP1 | −1.94144 | 0.046502254 |
| MPZL1 | −1.94084 | 0.020671596 |
| HDLBP | −1.938 | 0.040525091 |
| VKORC1L1 | −1.92651 | 0.028536059 |
| OCRL | −1.8641 | 0.049889138 |
| IMPAD1 | −1.83155 | 0.042443384 |
| REEP3 | −1.82779 | 0.038508624 |
| CCND1 | −1.78629 | 0.044005909 |

TABLE 7

Genes upregulated in progression versus baseline in converters

| Gene | log2 fold change | p adjusted |
|---|---|---|
| SYNE2 | 1.76486 | 0.035090697 |
| KLHL5 | 1.953712 | 0.043255466 |
| SEMA4D | 2.039621 | 0.047939776 |
| GPCPD1 | 2.043504 | 0.024547033 |
| ZFP36L1 | 2.094277 | 0.030147062 |
| LMO4 | 2.118286 | 0.043806646 |
| VAMP8 | 2.152774 | 0.025719884 |
| MAML2 | 2.161568 | 0.013457395 |
| SGPP2 | 2.172475 | 0.038933819 |
| EVL | 2.174487 | 0.03069022 |
| ARL4C | 2.289298 | 0.02065813 |
| ZNF594 | 2.370558 | 0.024441058 |
| ADGRE5 | 2.378299 | 0.037724978 |
| TCIRG1 | 2.401484 | 0.011482303 |
| ITPRIP | 2.407407 | 0.043553594 |
| ARNTL2 | 2.416197 | 0.027552182 |
| STAB1 | 2.442451 | 0.041153521 |
| ACSL5 | 2.449859 | 0.032607087 |
| STARD9 | 2.461366 | 0.014178131 |
| CNTRL | 2.46191 | 0.045896017 |
| C14orf159 | 2.468725 | 0.018386116 |
| MTSS1 | 2.478498 | 0.014262051 |
| DEF6 | 2.499426 | 0.032900387 |
| DGKA | 2.514621 | 0.010793965 |
| MOXD1 | 2.524514 | 0.029953046 |
| MEIS2 | 2.559851 | 0.047759085 |
| PSTPIP2 | 2.560933 | 0.013128708 |
| MCM5 | 2.57305 | 0.043299512 |
| PKIG | 2.598548 | 0.037724978 |
| ARRDC2 | 2.602361 | 0.042466454 |
| YPEL3 | 2.607879 | 0.04280022 |
| LAT2 | 2.616305 | 0.010142873 |
| SLCO2B1 | 2.620583 | 0.039065825 |
| PLEKHG1 | 2.622 | 0.017336922 |
| SHKBP1 | 2.627676 | 0.017873352 |
| STARD4 | 2.64387 | 0.048850161 |
| RP11-1299A16.3 | 2.644352 | 0.023760359 |
| TNFAIP3 | 2.651714 | 0.025827419 |
| TLR4 | 2.65947 | 0.046755101 |
| SYT11 | 2.676304 | 0.045777071 |
| TYMP | 2.688109 | 0.044415341 |
| PAQR8 | 2.700525 | 0.014508082 |
| CDCA7L | 2.714444 | 0.014508082 |
| ADCY7 | 2.721396 | 0.044154503 |
| U2AF1L4 | 2.725863 | 0.011060633 |
| TNFAIP2 | 2.73051 | 0.003816972 |
| TCF4 | 2.732309 | 0.000343767 |
| ID2 | 2.739049 | 0.022651032 |
| EPM2A | 2.743283 | 0.038516516 |
| AKNA | 2.743529 | 0.042253141 |

TABLE 7-continued

Genes upregulated in progression versus baseline in converters

| Gene | log2 fold change | p adjusted |
|---|---|---|
| FMNL1 | 2.754205 | 0.009188572 |
| PTPN6 | 2.757803 | 0.008421801 |
| ST6GAL1 | 2.78658 | 0.00063903 |
| TCF7L1 | 2.794273 | 0.040070983 |
| NAV2 | 2.807755 | 0.044005909 |
| ITGB8 | 2.848144 | 0.011752953 |
| UPP1 | 2.851644 | 0.029656097 |
| SYK | 2.859829 | 0.000248805 |
| SLFN12 | 2.877584 | 0.028362793 |
| CTC-479C5.12 | 2.900119 | 0.02055777 |
| CA13 | 2.940601 | 0.044905651 |
| PITPNC1 | 2.95736 | 0.018386116 |
| BTN2A2 | 2.963709 | 0.01146888 |
| RELT | 2.967281 | 0.021267136 |
| SIPA1 | 2.978846 | 0.025151796 |
| VSIR | 3.043285 | 0.032521008 |
| CCDC88A | 3.062236 | 0.034902216 |
| PRSS12 | 3.065974 | 0.033794109 |
| SEMA7A | 3.069592 | 0.043147437 |
| PTPRE | 3.073594 | 0.000197808 |
| IFI27 | 3.076778 | 0.029073077 |
| NEDD9 | 3.082863 | 0.024449839 |
| HOXA7 | 3.094877 | 0.047774263 |
| RP4-530I15.9 | 3.108511 | 0.012075274 |
| TNFRSF14 | 3.112997 | 0.00286168 |
| ELF4 | 3.145261 | 0.006126734 |
| APOBEC3C | 3.199642 | 0.013229426 |
| ESR2 | 3.210163 | 0.044005909 |
| FAM46C | 3.216277 | 0.000341157 |
| HLA-DRB1 | 3.216307 | 0.042698538 |
| APOBEC3B | 3.24095 | 0.00654894 |
| ATG16L2 | 3.263998 | 0.002310415 |
| CD83 | 3.264546 | 0.019840929 |
| ST3GAL5 | 3.267786 | 0.017269032 |
| DOCK11 | 3.275624 | 0.005833148 |
| FRMD3 | 3.278979 | 0.008748307 |
| RP11-477J21.7 | 3.280732 | 0.013128708 |
| IER5 | 3.283344 | 0.0071878 |
| TMEM108 | 3.284225 | 0.027194057 |
| SYNE3 | 3.303503 | 0.003024252 |
| GAB3 | 3.306265 | 0.035832408 |
| HMOX1 | 3.306551 | 7.52101E−05 |
| ADORA2A | 3.325043 | 0.011591857 |
| LAT | 3.337894 | 0.017085905 |
| ISG20 | 3.387287 | 0.003315309 |
| RP11-179F17.5 | 3.399836 | 0.037150016 |
| HCP5 | 3.400245 | 0.006613418 |
| ABCA7 | 3.404192 | 0.048240855 |
| NELL2 | 3.407317 | 0.045011864 |
| HVCN1 | 3.407787 | 0.04988753 |
| PLA2G4A | 3.410014 | 0.033450607 |
| PIM2 | 3.420993 | 0.039300584 |
| RBM38 | 3.425395 | 0.000343046 |
| TNFSF8 | 3.445471 | 0.025371608 |
| CIITA | 3.480644 | 0.045400538 |
| KYNU | 3.484213 | 0.047759085 |
| EGR3 | 3.487496 | 0.020111479 |
| TMEM176B | 3.489939 | 0.025330397 |
| RP11-164J13.1 | 3.498782 | 0.045896017 |
| TP63 | 3.505751 | 0.042265791 |
| ADA | 3.519396 | 0.000188397 |
| NCF4 | 3.535008 | 0.040822726 |
| CASP1 | 3.555885 | 0.038266611 |
| TCN2 | 3.564498 | 0.022784159 |
| RP11-705C15.3 | 3.569411 | 0.003699142 |
| CELF2 | 3.571699 | 0.006305434 |
| MPIG6B | 3.57175 | 0.031891577 |
| IGFLR1 | 3.572793 | 0.00128513 |
| FRY | 3.580113 | 0.016568111 |
| RP11-705C15.2 | 3.588493 | 0.006004447 |
| RGS18 | 3.603901 | 0.017227688 |
| SIRPB2 | 3.60667 | 0.044406444 |
| SLC38A1 | 3.609587 | 0.034227565 |
| CCL5 | 3.634047 | 0.027908918 |
| JAK3 | 3.647069 | 0.033129051 |

TABLE 7-continued

Genes upregulated in progression versus baseline in converters

| Gene | log2 fold change | p adjusted |
|---|---|---|
| RP11-493L12.2 | 3.659467 | 0.02627901 |
| TRIM22 | 3.664944 | 0.029649201 |
| POU2F2 | 3.667907 | 0.01146888 |
| APOL3 | 3.689628 | 0.04803082 |
| SERPINB1 | 3.698872 | 0.000258057 |
| CP | 3.712217 | 0.001704088 |
| ALDH1A1 | 3.728521 | 0.006821156 |
| RP11-448G15.3 | 3.729897 | 0.03330558 |
| IL16 | 3.730451 | 0.046150031 |
| PLEKHA2 | 3.730878 | 0.001917887 |
| CYBA | 3.736414 | 0.010734603 |
| MVP | 3.738595 | 0.000201104 |
| RP11-330H6.5 | 3.750256 | 0.012244921 |
| RP11-326I11.5 | 3.772997 | 0.042253141 |
| RP11-572O17.1 | 3.784717 | 0.025719884 |
| RGPD1 | 3.792267 | 0.001585598 |
| CTD-2516F10.2 | 3.79994 | 0.048963223 |
| GIMAP1 | 3.805483 | 0.007842689 |
| UCP2 | 3.806659 | 0.000215259 |
| HIST1H1D | 3.819261 | 0.034227565 |
| ETV5 | 3.845065 | 0.000140179 |
| CD37 | 3.870324 | 0.019522346 |
| PLEK | 3.880313 | 0.030503102 |
| SCN3A | 3.885338 | 0.043299512 |
| ITGAL | 3.913234 | 0.045774541 |
| ARHGAP9 | 3.920188 | 0.04246929 |
| CBFA2T3 | 3.925024 | 0.045258484 |
| RP11-750H9.5 | 3.934689 | 0.039637112 |
| CTD-2335A18.1 | 3.95795 | 0.042265791 |
| PTPRO | 3.96354 | 0.003841661 |
| TTC34 | 3.965547 | 0.038216068 |
| MIAT | 3.979853 | 5.00879E−06 |
| HOXA1 | 3.982865 | 0.045635625 |
| ARSJ | 3.987808 | 0.014537241 |
| CXCL12 | 3.98824 | 0.029656097 |
| XXbac-BPG299F13.17 | 4.000874 | 0.02064144 |
| ARHGAP4 | 4.012078 | 0.000403938 |
| CXCR3 | 4.021799 | 0.027594022 |
| ABC12-49244600F4.3 | 4.023337 | 0.016533393 |
| PTPRC | 4.032284 | 0.039415496 |
| CORO1A | 4.038029 | 0.000765875 |
| HLA-F | 4.040062 | 0.019243098 |
| WAS | 4.040803 | 0.006429423 |
| PARVG | 4.044891 | 0.001755056 |
| XCR1 | 4.049147 | 0.032521008 |
| LIMD2 | 4.060399 | 9.26563E−06 |
| LILRB1 | 4.068654 | 0.024445786 |
| PPP1R16B | 4.074227 | 0.025049208 |
| SERPINB9 | 4.078595 | 0.013050315 |
| KLRK1 | 4.084042 | 0.025767246 |
| CRIP1 | 4.103307 | 0.029596135 |
| GBP5 | 4.111995 | 0.044794635 |
| HLA-L | 4.119434 | 0.019674876 |
| AC074289.1 | 4.119841 | 0.030116743 |
| C1orf220 | 4.127487 | 0.00504242 |
| PYGL | 4.137146 | 4.65953E−06 |
| GVINP1 | 4.14692 | 0.037724978 |
| RP3-395M20.8 | 4.184878 | 0.041743802 |
| CD200R1 | 4.203766 | 0.037518287 |
| ADAM8 | 4.224928 | 0.001319505 |
| NCF1C | 4.226763 | 0.037724978 |
| RP11-44D15.3 | 4.237622 | 0.004597535 |
| PTPRCAP | 4.250074 | 0.016533393 |
| IL2RG | 4.250264 | 0.015406855 |
| CNTN1 | 4.263501 | 0.018865573 |
| PTGDS | 4.268047 | 0.025330397 |
| GPAT2 | 4.270703 | 0.047961416 |
| PIK3CD | 4.296049 | 0.002299064 |
| MSC | 4.298519 | 0.042466454 |
| CR1 | 4.302019 | 0.030822155 |
| KLRD1 | 4.3059 | 0.036190951 |
| RP11-426C22.10 | 4.3261 | 0.017438053 |
| IKZF1 | 4.347873 | 0.028347515 |
| S100A6 | 4.358014 | 8.39035E−05 |
| PKD1L3 | 4.38512 | 0.005930687 |

TABLE 7-continued

Genes upregulated in progression versus baseline in converters

| Gene | log2 fold change | p adjusted |
|---|---|---|
| CD8B | 4.390215 | 0.011509461 |
| TRBC1 | 4.417117 | 0.023814858 |
| ATP2A3 | 4.421924 | 0.001266179 |
| ARL11 | 4.44472 | 0.00175777 |
| AMICA1 | 4.450267 | 0.030974193 |
| CACNA1E | 4.460603 | 0.020292054 |
| CTB-118N6.3 | 4.469907 | 0.021713608 |
| AC007254.3 | 4.477776 | 0.027161703 |
| CCDC141 | 4.496443 | 0.009479687 |
| PTHLH | 4.498621 | 0.009550388 |
| DAPP1 | 4.50607 | 0.030116743 |
| GZMK | 4.512197 | 0.009188572 |
| CD247 | 4.518303 | 0.015768631 |
| IL21R | 4.526217 | 0.003312989 |
| CD40 | 4.535153 | 0.018874524 |
| ABCB4 | 4.560807 | 0.025719884 |
| WDFY4 | 4.563862 | 0.000666033 |
| IL8RBP | 4.599721 | 0.001509204 |
| MICB | 4.612005 | 0.000878147 |
| CYTIP | 4.612133 | 0.015950048 |
| IL24 | 4.613578 | 0.006307743 |
| CARD11 | 4.615195 | 0.025719884 |
| GZMH | 4.618429 | 0.046061386 |
| FGD2 | 4.637003 | 0.00278874 |
| RHOH | 4.640321 | 0.018131052 |
| DHRS9 | 4.671261 | 0.001580651 |
| PRF1 | 4.672126 | 0.012075274 |
| TMEM176A | 4.672206 | 0.001024203 |
| IL7R | 4.674792 | 0.008748307 |
| HAPLN3 | 4.706129 | 0.008442538 |
| SOCS1 | 4.709079 | 0.016854272 |
| RP11-373L24.1 | 4.727501 | 2.13211E−05 |
| PRTFDC1 | 4.733108 | 0.010436503 |
| FCGR2B | 4.741864 | 0.016003685 |
| GPSM3 | 4.75138 | 4.28042E−06 |
| IKZF3 | 4.754905 | 0.010816456 |
| DGKG | 4.758519 | 0.000145626 |
| RP5-1171I10.5 | 4.765969 | 0.001053877 |
| GCSAM | 4.772512 | 0.010412188 |
| CERKL | 4.783274 | 0.016668672 |
| RP11-392O17.1 | 4.827101 | 0.017992065 |
| CD3E | 4.830298 | 0.012860179 |
| CD96 | 4.832592 | 0.008081538 |
| PAX5 | 4.840024 | 0.004346743 |
| HACD1 | 4.842557 | 0.031124974 |
| CLEC2D | 4.852645 | 0.009777346 |
| TNFSF11 | 4.861492 | 0.034395134 |
| ROBO3 | 4.862121 | 0.048367317 |
| DMRTA1 | 4.862152 | 0.045896017 |
| TMC8 | 4.87507 | 0.00038781 |
| TIMD4 | 4.880279 | 0.02232107 |
| TMEM163 | 4.90377 | 0.001585598 |
| ITK | 4.906544 | 0.010575746 |
| LRMP | 4.908943 | 0.020599231 |
| CEMIP | 4.921437 | 0.003886897 |
| FSTL5 | 4.92619 | 0.025299271 |
| MEI1 | 4.932381 | 0.022426113 |
| PROX1 | 4.952832 | 2.13476E−11 |
| ZNF826P | 4.962978 | 0.029303804 |
| RP11-358M11.2 | 4.965878 | 0.001986346 |
| CD52 | 4.971075 | 0.002229025 |
| GAPT | 4.981553 | 0.027794701 |
| NOD2 | 4.990199 | 0.000808035 |
| HBB | 5.003826 | 0.024445786 |
| CD274 | 5.006322 | 0.018382137 |
| PLCG2 | 5.027363 | 0.005303591 |
| LINC00528 | 5.061849 | 0.032755633 |
| RP11-61F12.1 | 5.075263 | 0.003315652 |
| LA16c-60D12.2 | 5.093703 | 0.049085362 |
| IRF8 | 5.099649 | 0.014413916 |
| SLAMF1 | 5.106551 | 0.00271796 |
| RP11-622O11.2 | 5.132995 | 0.013484008 |
| ANO9 | 5.16333 | 0.004666712 |
| SLAMF6 | 5.166919 | 0.020594204 |
| AC005618.6 | 5.187865 | 0.006599332 |

TABLE 7-continued

Genes upregulated in progression versus baseline in converters

| Gene | log2 fold change | p adjusted |
|---|---|---|
| RP11-398A8.3 | 5.189684 | 0.027061508 |
| SLFN13 | 5.193984 | 0.021381984 |
| KIAA0226L | 5.194888 | 0.019923058 |
| CD48 | 5.195172 | 0.023189266 |
| GRAPL | 5.202015 | 0.036190951 |
| TRBC2 | 5.214755 | 0.006941479 |
| KMO | 5.216515 | 0.01699022 |
| FPR1 | 5.222859 | 0.00060063 |
| TDGF1 | 5.258904 | 0.003347226 |
| KCNH8 | 5.270464 | 0.012123472 |
| RNF183 | 5.287347 | 0.025330397 |
| THEMIS | 5.314463 | 7.31986E−05 |
| LILRA1 | 5.316085 | 0.027314987 |
| AC020951.1 | 5.3282 | 0.030441497 |
| ZAP70 | 5.331009 | 0.006614271 |
| IGKV1-39 | 5.335583 | 0.036732713 |
| CD3D | 5.378953 | 0.018040726 |
| PRKCB | 5.41952 | 0.001844778 |
| SDPR | 5.424391 | 0.008815765 |
| CD79B | 5.434795 | 0.02065813 |
| RP11-500C11.3 | 5.446435 | 0.042698538 |
| DTHD1 | 5.461362 | 0.032653896 |
| RP11-981G7.6 | 5.472291 | 0.001225053 |
| HK3 | 5.488422 | 0.006542022 |
| VNN2 | 5.491846 | 0.002273087 |
| PSTPIP1 | 5.506408 | 0.020600986 |
| SLC2A6 | 5.511201 | 0.003315309 |
| AC079767.4 | 5.516876 | 0.012010138 |
| FCMR | 5.527526 | 0.000722156 |
| S100A8 | 5.538629 | 0.001485163 |
| RP11-25K21.4 | 5.561899 | 0.010183334 |
| PYHIN1 | 5.563373 | 0.004546655 |
| CTSW | 5.590185 | 1.83635E−05 |
| RP5-1071N3.1 | 5.604375 | 0.039300584 |
| GS1-410F4.2 | 5.614201 | 0.04138386 |
| SLC9A4 | 5.624641 | 0.000879387 |
| ZNF804A | 5.63363 | 0.000343767 |
| RIPOR2 | 5.63582 | 0.001704088 |
| SNX20 | 5.65417 | 0.013451075 |
| DTX2P1 | 5.655218 | 0.026149898 |
| GFI1 | 5.655476 | 0.005696984 |
| IRF4 | 5.676647 | 0.006519301 |
| ALDH3A1 | 5.681413 | 0.042265791 |
| CD22 | 5.682041 | 0.024185663 |
| LY9 | 5.684414 | 0.011082838 |
| GPR174 | 5.691891 | 0.003841661 |
| LAX1 | 5.7163 | 0.027196875 |
| RP11-960L18.1 | 5.747223 | 0.032581945 |
| PDE6G | 5.74771 | 0.043299512 |
| TOX | 5.751318 | 7.61414E−06 |
| CTD-2020K17.1 | 5.767422 | 0.023420869 |
| ENPP6 | 5.803448 | 0.025465136 |
| P2RY10 | 5.811183 | 0.004856004 |
| ADIRF-AS1 | 5.813772 | 0.003365526 |
| PCDH15 | 5.821008 | 0.045258484 |
| BCL11A | 5.844474 | 3.17619E−05 |
| HCST | 5.853444 | 0.012860179 |
| XXbac-BPG254F23.5 | 5.873496 | 0.032883497 |
| HLA-DOB | 5.947486 | 0.003495868 |
| BACH2 | 6.002756 | 5.80941E−05 |
| MAP4K1 | 6.042082 | 0.000722156 |
| HBA1 | 6.046695 | 0.012253862 |
| RP3-351K20.4 | 6.077065 | 0.016568111 |
| MMP12 | 6.13847 | 0.012089491 |
| GPR158 | 6.140182 | 0.04712138 |
| POF1B | 6.149312 | 0.002986091 |
| TMEM156 | 6.153658 | 0.016533393 |
| RP4-647C14.2 | 6.156388 | 0.037559431 |
| RP6-99M1.2 | 6.194159 | 0.000110269 |
| RP11-327F22.1 | 6.246517 | 0.009443348 |
| RP11-211N8.2 | 6.266561 | 0.034227565 |
| RP11-460N11.2 | 6.318951 | 0.013942832 |
| SIT1 | 6.349488 | 0.000698766 |
| TNFRSF13C | 6.350606 | 1.95165E−10 |
| RP11-808N1.1 | 6.401373 | 0.000457098 |

TABLE 7-continued

Genes upregulated in progression versus baseline in converters

| Gene | log2 fold change | p adjusted |
|---|---|---|
| BNIP3P4 | 6.413333 | 0.000411631 |
| GIMAP5 | 6.418087 | 0.002543297 |
| C6orf141 | 6.440189 | 0.006170538 |
| RP11-374F3.4 | 6.468822 | 0.005108237 |
| RP1-56K13.1 | 6.480663 | 0.001319505 |
| FCRL3 | 6.525075 | 0.000682541 |
| IGHD | 6.569965 | 0.046150031 |
| NKG7 | 6.641471 | 7.09926E−06 |
| BLK | 6.664237 | 0.012515436 |
| UGT8 | 6.669688 | 2.08596E−05 |
| VPREB3 | 6.813197 | 0.021600758 |
| NAPSB | 6.85327 | 1.54075E−05 |
| APOBEC3D | 6.878752 | 5.009E−05 |
| TLR10 | 6.927124 | 0.003095416 |
| CD79A | 6.955214 | 1.06305E−05 |
| AC104820.2 | 6.958632 | 0.01146888 |
| CD27 | 6.961762 | 0.000343767 |
| PARP15 | 6.962248 | 0.000589813 |
| CD72 | 7.000245 | 3.23698E−06 |
| PROX1-AS1 | 7.006641 | 0.016010283 |
| CLNK | 7.013311 | 0.039825295 |
| POU2AF1 | 7.033135 | 0.001704088 |
| AQP9 | 7.045749 | 1.23629E−05 |
| CHL1 | 7.064701 | 2.6622E−09 |
| FAM159A | 7.069956 | 0.002299064 |
| AC012123.1 | 7.084507 | 0.030147062 |
| UBD | 7.085966 | 0.000108511 |
| CTC-260E6.4 | 7.093282 | 0.019522346 |
| TCL6 | 7.098081 | 0.000686703 |
| RP11-1399P15.1 | 7.149517 | 0.046710982 |
| RP11-374F3.5 | 7.173119 | 0.018476895 |
| C11orf21 | 7.19384 | 0.004551851 |
| WDR49 | 7.224185 | 0.014225089 |
| ZC3H12D | 7.236843 | 0.001350943 |
| OR2I1P | 7.260115 | 0.000158632 |
| RP4-671O14.5 | 7.302321 | 0.00033472 |
| RASGRF1 | 7.342961 | 0.001592099 |
| CTC-260E6.6 | 7.343644 | 0.010427639 |
| C10orf31 | 7.368453 | 0.004735077 |
| CTAGE6 | 7.397778 | 0.00997142 |
| AC090627.1 | 7.492274 | 0.006725243 |
| SP140 | 7.496913 | 0.000166107 |
| RP1-66N13.3 | 7.515983 | 0.043299512 |
| IFNG | 7.550884 | 0.04988753 |
| PPBP | 7.57855 | 0.01812717 |
| FCRLA | 7.596083 | 0.001107258 |
| RP11-325F22.2 | 7.596515 | 0.029649201 |
| CLEC17A | 7.689823 | 0.029649201 |
| CD5L | 7.723779 | 0.010734603 |
| RP11-445F6.2 | 7.754531 | 0.011247681 |
| CLECL1 | 7.791782 | 0.002844035 |
| TNFRSF13B | 7.911565 | 0.013363493 |
| KLRC4-KLRK1 | 7.97333 | 0.015873475 |
| KLHL14 | 8.048069 | 0.000326698 |
| TLR9 | 8.089038 | 0.006777866 |
| RP11-553L6.2 | 8.143238 | 0.001291421 |
| SPIB | 8.183422 | 0.000120069 |
| CD1C | 8.197458 | 0.019064569 |
| TIFAB | 8.242314 | 0.011082838 |
| AC002480.5 | 8.254084 | 0.014004416 |
| GZMB | 8.286565 | 0.000292658 |
| RP11-861A13.4 | 8.329228 | 8.10582E−05 |
| IDO1 | 8.513727 | 0.000546018 |
| ZNF831 | 8.903011 | 0.000248055 |
| RP11-1143G9.4 | 9.531873 | 2.43639E−07 |
| MS4A1 | 9.902964 | 0.016533393 |
| CCR7 | 10.0602 | 1.08457E−06 |
| CXCL13 | 10.46714 | 0.040861189 |
| BTLA | 10.85143 | 0.047656045 |

TABLE 8

| Gene signature composition | | | |
|---|---|---|---|
| Beltran, et al. NEPC Up | Zhang, et al. Basal | Kim, et al. AR-repressed | ARG10 |
| ASXL3 | COL17A1 | NRXN3 | ALDH1A3 |
| AURKA | CSMD2 | ALX4 | KLK3 |
| BRINP1 | CDH13 | TRAF3IP2 | FKBP5 |
| C7orf76 | MUM1L1 | ATP2C2 | KLK2 |
| CAND2 | MMP3 | KDM4A | NKX3-1 |
| DNMT1 | IL33 | TGFBR3 | TMPRSS2 |
| ETV5 | GIMAP8 | SEMA3C | PLPP1 |
| EZH2 | PDPN | RBL1 | PART1 |
| GNAO1 | VSNL1 | MET | PMEPA1 |
| GPX2 | BNC1 | CIT | STEAP4 |
| JAKMIP2 | IGFBP7 | CHAC1 | |
| KCNB2 | DLK2 | CABLES1 | |
| KCND2 | HMGA2 | FLNB | |
| KIAA0408 | NOTCH4 | DAB2IP | |
| LRRC16B | THBS2 | AUTS2 | |
| MAP10 | TAGLN | DAB1 | |
| MYCN | FHL1 | CDC42EP4 | |
| NRSN1 | ANXA8L2 | CD55 | |
| PCSK1 | COL4A6 | TTLL3 | |
| PROX1 | KCNQ5 | RP11-159F24.1 | |
| RGS7 | WNT7A | MYO15B | |
| SCG3 | KCNMA1 | BCLAF1 | |
| SEC11C | NIPAL4 | RIMS1 | |
| SEZ6 | FLRT2 | NEFL | |
| SOGA3 | LTBP2 | GPD2 | |
| ST8SIA3 | FOXI1 | HPCAL4 | |
| SVOP | NGFR | SCRN1 | |
| SYT11 | SERPINB13 | TACC2 | |
| TRIM9 | CNTNAP3B | APBB2 | |
| | FGFR3 | CDCA7L | |
| | ARHGAP25 | GABRA5 | |
| | AEBP1 | MGST1 | |
| | FJX1 | DPF1 | |
| | TNC | RAI14 | |
| | MSRB3 | PARP12 | |
| | NRG1 | PLXNA2 | |
| | SERPINF1 | EPB41L2 | |
| | DLC1 | IGSF9B | |
| | IL1A | RCOR1 | |
| | DKK3 | SMAD7 | |
| | ERG | MAP2K6 | |
| | SYNE1 | FHOD3 | |
| | JAG2 | BIN1 | |
| | JAM3 | TMOD1 | |
| | MRC2 | SMAD6 | |
| | SPARC | DUSP5 | |
| | C16orf74 | HUNK | |
| | FAT3 | MYO10 | |
| | KIRREL | CXorf57 | |
| | SH2D5 | SMC6 | |
| | KRT6A | ARHGEF3 | |
| | KRT34 | STRBP | |
| | ITGA6 | STXBP6 | |
| | TP63 | ROBO1 | |
| | KRT5 | TANC2 | |
| | KRT14 | FRMD3 | |
| | | GOLIM4 | |
| | | DPP10 | |
| | | WSCD1 | |
| | | TNFAIP2 | |
| | | EPHA6 | |
| | | SH3GL2 | |
| | | BCL2 | |
| | | BEND3 | |
| | | MBP | |
| | | SAMD5 | |
| | | TMEM65 | |
| | | MYB | |
| | | ASXL2 | |
| | | HRH2 | |
| | | KIAA0319 | |
| | | CREB5 | |
| | | AK5 | |
| | | PALM2-AKAP2 | |
| | | IKZF3 | |
| | | ARHGEF28 | |

REFERENCES

1. Attard, G., et al. Phase I clinical trial of a selective inhibitor of CYP17, abiraterone acetate, confirms that castration-resistant prostate cancer commonly remains hormone driven. J Clin Oncol 26, 4563-4571 (2008).
2. Clegg, N. J., et al. ARN-509: a novel antiandrogen for prostate cancer treatment. Cancer Res 72, 1494-1503 (2012).
3. Scher, H. I., et al. Antitumour activity of MDV3100 in castration-resistant prostate cancer: a phase 1-2 study. Lancet 375, 1437-1446 (2010).
4. Tran, C., et al. Development of a second-generation antiandrogen for treatment of advanced prostate cancer. Science 324, 787-790 (2009).
5. Swami, U., McFarland, T. R., Nussenzveig, R. & Agarwal, N. Advanced Prostate Cancer: Treatment Advances and Future Directions. Trends Cancer (2020).
6. Beer, T. M., et al. Enzalutamide in metastatic prostate cancer before chemotherapy. N Engl J Med 371, 424-433 (2014).
7. Scher, H. I., et al. Increased survival with enzalutamide in prostate cancer after chemotherapy. N Engl J Med 367, 1187-1197 (2012).
8. Armstrong, A. J., et al. ARCHES: A Randomized, Phase III Study of Androgen Deprivation Therapy With Enzalutamide or Placebo in Men With Metastatic Hormone-Sensitive Prostate Cancer. J Clin Oncol 37, 2974-2986 (2019).
9. Davis, I. D., et al. Enzalutamide with Standard First-Line Therapy in Metastatic Prostate Cancer. N Engl J Med 381, 121-131 (2019).
10. Abida, W., et al. Genomic correlates of clinical outcome in advanced prostate cancer. Proc Natl Acad Sci USA 116, 11428-11436 (2019).
11. Annala, M., et al. Circulating Tumor DNA Genomics Correlate with Resistance to Abiraterone and Enzalutamide in Prostate Cancer. Cancer Discov 8, 444-457 (2018).
12. Armstrong, A. J., et al. Prospective Multicenter Study of Circulating Tumor Cell AR-V7 and Taxane Versus Hormonal Treatment Outcomes in Metastatic Castration-Resistant Prostate Cancer. JCO Precis Oncol 4(2020).
13. McKay, R. R., et al. Phase II Multicenter Study of Enzalutamide in Metastatic Castration-Resistant Prostate Cancer to Identify Mechanisms Driving Resistance. Clin Cancer Res 27, 3610-3619 (2021).
14. Chen, W. S., et al. Genomic Drivers of Poor Prognosis and Enzalutamide Resistance in Metastatic Castration-resistant Prostate Cancer. Eur Urol 76, 562-571 (2019).

He, M. X., et al. Transcriptional mediators of treatment resistance in lethal prostate cancer. Nat Med 27, 426-433 (2021).

16. Miyamoto, D. T., et al. RNA-Seq of single prostate CTCs implicates noncanonical Wnt signaling in antiandrogen resistance. Science 349, 1351-1356 (2015).

17. Pal, S. K., et al. Identification of mechanisms of resistance to treatment with abiraterone acetate or enzalutamide in patients with castration-resistant prostate cancer (CRPC). Cancer 124, 1216-1224 (2018).
18. Alumkal, J. J., et al. Transcriptional profiling identifies an androgen receptor activity-low, stemness program associated with enzalutamide resistance. Proc Natl Acad Sci USA 117, 12315-12323 (2020).
19. Bluemn, E. G., et al. Androgen Receptor Pathway-Independent Prostate Cancer Is Sustained through FGF Signaling. Cancer Cell 32, 474-489 e476 (2017).
20. Beltran, H., et al. The role of lineage plasticity in prostate cancer therapy resistance. Clin Cancer Res (2019).
21. Abdulfatah, E., et al. De novo neuroendocrine transdifferentiation in primary prostate cancer-a phenotype associated with advanced clinico-pathologic features and aggressive outcome. Med Oncol 38, 26 (2021).
22. Beltran, H., et al. Divergent clonal evolution of castration-resistant neuroendocrine prostate cancer. Nat Med 22, 298-305 (2016).
23. Lin, D., et al. High fidelity patient-derived xenografts for accelerating prostate cancer discovery and drug development. Cancer Res 74, 1272-1283 (2014).
24. Labrecque, M. P., et al. Molecular profiling stratifies diverse phenotypes of treatment-refractory metastatic castration-resistant prostate cancer. J Clin Invest 129, 4492-4505 (2019).
25. Aggarwal, R., et al. Clinical and Genomic Characterization of Treatment-Emergent Small-Cell Neuroendocrine Prostate Cancer: A Multi-institutional Prospective Study. J Clin Oncol 36, 2492-2503 (2018).
26. Alvarez, M. J., et al. Functional characterization of somatic mutations in cancer using network-based inference of protein activity. Nat Genet 48, 838-847 (2016).
27. Nyquist, M. D., et al. Combined TP53 and RB1 Loss Promotes Prostate Cancer Resistance to a Spectrum of Therapeutics and Confers Vulnerability to Replication Stress. Cell Rep 31, 107669 (2020).
28. Zhang, D., et al. Stem cell and neurogenic gene-expression profiles link prostate basal cells to aggressive prostate cancer. Nat Commun 7, 10798 (2016).
29. Kim, D. H., et al. BET Bromodomain Inhibition Blocks an AR-Repressed, E2F1-Activated Treatment-Emergent Neuroendocrine Prostate Cancer Lineage Plasticity Program. Clin Cancer Res 27, 4923-4936 (2021).
30. Ku, S. Y., et al. Rb1 and Trp53 cooperate to suppress prostate cancer lineage plasticity, metastasis, and antiandrogen resistance. Science 355, 78-83 (2017).
31. Mu, P., et al. SOX2 promotes lineage plasticity and antiandrogen resistance in TP53- and RB1-deficient prostate cancer. Science 355, 84-88 (2017).
32. Yu, J., et al. The Functional Landscape of Patient-Derived RNF43 Mutations Predicts
Sensitivity to Wnt Inhibition. Cancer Res 80, 5619-5632 (2020).
33. Zhang, X., et al. Tikil is required for head formation via Wnt cleavage-oxidation and inactivation. Cell 149, 1565-1577 (2012).
34. Ge, J., et al. Ubiquitin carboxyl-terminal hydrolase isozyme L5 inhibits human glioma cell migration and invasion via downregulating SNRPF. Oncotarget 8, 113635-113649 (2017).
35. Rak, M. & Rustin, P. Supernumerary subunits NDUFA3, NDUFAS and NDUFA12 are required for the formation of the extramembrane arm of human mitochondrial complex I. FEBS Lett 588, 1832-1838 (2014).
36. Guan, S. S., Sheu, M. L., Wu, C. T., Chiang, C. K. & Liu, S. H. ATP synthase subunit-beta down-regulation aggravates diabetic nephropathy. Sci Rep 5, 14561 (2015).
37. Wang, Y., et al. Molecular events in neuroendocrine prostate cancer development. Nat Rev Urol 18, 581-596 (2021).
38. Xin, Z., et al. Insulinoma-associated protein 1 is a novel sensitive and specific marker for small cell carcinoma of the prostate. Hum Pathol 79, 151-159 (2018).
39. Labrecque, M. P., et al. Molecular profiling stratifies diverse phenotypes of treatment-refractory metastatic castration-resistant prostate cancer. J Clin Invest 130(2019).
40. Yamashina, T., et al. Cancer stem-like cells derived from chemoresistant tumors have a unique capacity to prime tumorigenic myeloid cells. Cancer Res 74, 2698-2709 (2014).
41. Lo, U. G., et al. IFNgamma-Induced IFITS Promotes Epithelial-to-Mesenchymal Transition in Prostate Cancer via miRNA Processing. Cancer Res 79, 1098-1112 (2019).
42. Donehower, L. A., et al. Integrated Analysis of TP53 Gene and Pathway Alterations in The Cancer Genome Atlas. Cell Rep 28, 1370-1384 e1375 (2019).
43. Chen, W. S., et al. Novel RB1-Loss Transcriptomic Signature Is Associated with Poor Clinical Outcomes across Cancer Types. Clin Cancer Res 25, 4290-4299 (2019).
44. Lee, J. K., et al. N-Myc Drives Neuroendocrine Prostate Cancer Initiated from Human Prostate Epithelial Cells. Cancer Cell 29, 536-547 (2016).
45. Aggarwal, R. R., et al. A Phase Ib/IIa Study of the Pan-BET Inhibitor ZEN-3694 in Combination with Enzalutamide in Patients with Metastatic Castration-resistant Prostate Cancer. Clin Cancer Res 26, 5338-5347 (2020).
46. Penson, D. F., et al. Enzalutamide Versus Bicalutamide in Castration-Resistant Prostate Cancer: The STRIVE Trial. J Clin Oncol 34, 2098-2106 (2016).
47. Shore, N. D., et al. Efficacy and safety of enzalutamide versus bicalutamide for patients with metastatic prostate cancer (TERRAIN): a randomised, double-blind, phase 2 study. Lancet Oncol 17, 153-163 (2016).
48. Tao, D. L., et al. Molecular Testing in Patients With Castration-Resistant Prostate Cancer and Its Impact on Clinical Decision Making. JCO Precision Oncology, 1-11 (2017).
49. Foye, A. & Febbo, P. G. Cancer gene profiling in prostate cancer. Methods Mol Biol 576, 293-326 (2010).
50. Li, B. & Dewey, C. N. RSEM: accurate transcript quantification from RNA-Seq data with or without a reference genome. BMC Bioinformatics 12, 323 (2011).
51. Love, M. I., Huber, W. & Anders, S. Moderated estimation of fold change and dispersion for RNA-seq data with DESeq2. Genome Biol 15, 550 (2014).
52. Wu, D. & Smyth, G. K. Camera: a competitive gene set test accounting for inter-gene correlation. Nucleic Acids Res 40, e133 (2012).
53. Lefebvre, C., et al. A human B-cell interactome identifies MYB and FOXM1 as master regulators of proliferation in germinal centers. Mol Syst Biol 6, 377 (2010).
54. Robertson, A. G., et al. Integrative Analysis Identifies Four Molecular and Clinical Subsets in Uveal Melanoma. Cancer Cell 32, 204-220 e215 (2017).
55. Cejas, P., et al. Subtype heterogeneity and epigenetic convergence in neuroendocrine prostate cancer. Nat Commun 12, 5775 (2021).

56. Bankhead, P., et al. QuPath: Open source software for digital pathology image analysis. Sci Rep 7, 16878 (2017).
57. Grasso, C., et al. Assessing copy number alterations in targeted, amplicon-based next-generation sequencing data. J Mol Diagn 17, 53-63 (2015).
58. Hovelson, D. H., et al. Rapid, ultra low coverage copy number profiling of cell-free DNA as a precision oncology screening strategy. Oncotarget 8, 89848-89866 (2017).
59. Adalsteinsson, V. A., et al. Scalable whole-exome sequencing of cell-free DNA reveals high concordance with metastatic tumors. Nat Commun 8, 1324 (2017).
60. Hovelson, D. H., et al. Development and validation of a scalable next-generation sequencing system for assessing relevant somatic variants in solid tumors. Neoplasia 17, 385-399 (2015).

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the medical sciences are intended to be within the scope of the following claims.

The invention claimed is:

1. A method for treating prostate cancer, comprising:

a) assaying a sample from a subject diagnosed with prostate cancer for the level of expression of the genes RING FINGER PROTEIN 43 (RNF43), SMALL NUCLEAR RIBONUCLEOPROTEIN POLYPEPTIDE F (SNRPF), TRAB DOMAIN-CONTAINING PROTEIN 2A (TRABD2A), NADH-UBIQUINONE OXIDOREDUCTASE SUBUNIT A12 (NDUFA12), GROWTH ARREST-SPECIFIC 2-LIKE 3 (GAS2L3), RIBOSOMAL PROTEIN S24 (RPS24), DNA REPLICATION HELICASE/NUCLEASE 2 (DNA2), RETINITIS PIGMENTOSA (RP5-857K21.10), POC1 CENTRIOLAR PROTEIN B (POC1B), ADENOSINE KINASE (ADK), ATP SYNTHASE F1, SUBUNIT BETA (ATP5B), EXPORTIN, tRNA (XPOT), SOLUTE CARRIER ORGANIC ANION TRANSPORTER FAMILY, MEMBER 1B3 (SLCO1B3), and RHO-RELATED BTB DOMAIN-CONTAINING PROTEIN 1 (RHOBTB1);

b) calculating a lineage plasticity score based on said level of gene expression;

c) identifying the subject with a high lineage plasticity score; and d) administering treatment that does not include an androgen receptor signaling inhibitor treatment to said subject, wherein the treatment includes a prostate cancer treatment that is chemotherapy, radiation, surgery and/or immunotherapy.

2. A method for treating prostate cancer, comprising:

a) assaying a sample from a subject diagnosed with prostate cancer for the level of expression of the genes RNF43, SNRPF, TRABD2A, NDUFA12, GAS2L3, RPS24, DNA2, RP5-857K21.10, POC1B, ADK, ATP5B, XPOT, SLCO1B3, and RHOBTB1;

b) calculating a lineage plasticity score based on said level of gene expression;

c) identifying the subject with a low lineage plasticity score; and d) administering an androgen receptor signaling inhibitor treatment to said the subject.

3. The method of claim 2, wherein said treatment is enzalutamide.

4. The method of claim 1, wherein said prostate cancer is castration-resistant prostate cancer (CRPC).

5. The method of claim 1, wherein said sample is blood, urine, or prostate cells.

* * * * *